(12) United States Patent
Fotsch et al.

(10) Patent No.: US 8,041,579 B2
(45) Date of Patent: Oct. 18, 2011

(54) METHOD, SYSTEM AND ARTICLE OF MANUFACTURE, SUCH AS A CARD, TO PROVIDE USER SELECTABLE MEDICAL INFORMATION AND INFORMATION TO OBTAIN ELIGIBILITY OF HEALTHCARE PAYMENTS

(75) Inventors: Edward J. Fotsch, Sausalito, CA (US); Debra Del Guidice, Sausalito, CA (US)

(73) Assignee: Intuit Inc., Mountain View, CA (US)

( * ) Notice: Subject to any disclaimer, the term of this patent is extended or adjusted under 35 U.S.C. 154(b) by 1459 days.

(21) Appl. No.: 11/362,644

(22) Filed: Feb. 27, 2006

(65) Prior Publication Data

US 2006/0143052 A1 Jun. 29, 2006

Related U.S. Application Data

(63) Continuation-in-part of application No. 11/208,144, filed on Aug. 19, 2005, which is a continuation-in-part of application No. 11/085,984, filed on Mar. 21, 2005, and a continuation-in-part of application No. 10/641,982, filed on Aug. 15, 2003, now abandoned, which is a continuation-in-part of application No. 10/387,041, filed on Mar. 10, 2003, now abandoned.

(51) Int. Cl.
*G06Q 10/00* (2006.01)
*G06Q 50/00* (2006.01)
(52) U.S. Cl. .................. 705/2; 705/3; 600/300
(58) Field of Classification Search .............. 705/2–4; 600/300; 283/68, 117
See application file for complete search history.

(56) References Cited

U.S. PATENT DOCUMENTS 4,319,336 A 3/1982 Anderson et al.
4,650,981 A * 3/1987 Foletta ................... 235/449
(Continued)

OTHER PUBLICATIONS

International Search Report & The Written Opinion of the International Searching Authority, Patent Cooperation Treaty, Application No. PCT/US06/09968, Sep. 25, 2007.

(Continued)

*Primary Examiner* — Gerald J. O'Connor
*Assistant Examiner* — Linh Michelle Le
(74) *Attorney, Agent, or Firm* — Gunnison, McKay & Hodgson, L.L.P.; Philip McKay

(57) ABSTRACT

An article of manufacture, such as a credit card sized health card having a magnetic strip, includes user selected medical information and/or information to obtain medical information of an individual and eligibility of healthcare payments in an embodiment. A user may customize the medical information displayed on the health card. In an embodiment, a method obtains and stores medical information in a machine-readable format. An interface to select a portion of the medical information is provided to a user. In response to a user selection, the portion is displayed on a substrate, such as the health card, and the medical information is accessed by information, such as a URL, user identifier and password, recorded in a machine-readable format on the substrate. In an embodiment, a system includes a healthcare provider processing device obtaining eligibility information from the health card and generating an eligibility request to an entity processing device that forwards the eligibility request to a payer processing device. An eligibility response from the payer processing device is then provided to the healthcare provider processing device via the entity processing device. In an embodiment, medical information in a paper format is faxed using a unique user identifier and password and categorized into a machine-readable format.

8 Claims, 20 Drawing Sheets

U.S. PATENT DOCUMENTS

| | | | |
|---|---|---|---|
| 5,478,211 | A | 12/1995 | Dominiak et al. |
| 5,589,892 | A | 12/1996 | Knee et al. |
| 5,597,072 | A | 1/1997 | Lieberman et al. |
| 5,862,223 | A | 1/1999 | Walker et al. |
| 5,899,998 | A | 5/1999 | McGauley et al. |
| 5,930,759 | A * | 7/1999 | Moore et al. .................. 705/2 |
| 5,954,641 | A | 9/1999 | Kehr et al. |
| 5,974,389 | A | 10/1999 | Clark et al. |
| 6,039,688 | A | 3/2000 | Douglas et al. |
| 6,151,586 | A | 11/2000 | Brown |
| 6,171,112 | B1 | 1/2001 | Clark et al. |
| 6,208,973 | B1 * | 3/2001 | Boyer et al. .................. 705/2 |
| 6,272,472 | B1 | 8/2001 | Danneels et al. |
| 6,381,029 | B1 | 4/2002 | Tipirneni |
| 6,516,315 | B1 | 2/2003 | Gupta |
| 6,654,724 | B1 | 11/2003 | Rubin et al. |
| 6,988,075 | B1 | 1/2006 | Hacker |
| 7,174,368 | B2 | 2/2007 | Ross, Jr. |
| 2001/0056359 | A1 | 12/2001 | Abreu |
| 2002/0029157 | A1 | 3/2002 | Marchosky |
| 2002/0072934 | A1 * | 6/2002 | Ross et al. .................. 705/3 |
| 2002/0123909 | A1 | 9/2002 | Salisbury |
| 2002/0128865 | A1 | 9/2002 | Alten |
| 2002/0128870 | A1 | 9/2002 | Whitson |
| 2002/0138306 | A1 | 9/2002 | Sabovich |
| 2002/0156650 | A1 | 10/2002 | Klein et al. |
| 2003/0018495 | A1 * | 1/2003 | Sussman .................. 705/2 |
| 2003/0023269 | A1 | 1/2003 | den Boer |
| 2003/0023562 | A1 | 1/2003 | Bailey et al. |
| 2003/0028399 | A1 | 2/2003 | Davis et al. |
| 2003/0040940 | A1 | 2/2003 | Nehammer |
| 2003/0088440 | A1 | 5/2003 | Dunn |
| 2003/0088452 | A1 | 5/2003 | Kelly |
| 2003/0188200 | A1 | 10/2003 | Paquin et al. |
| 2003/0214630 | A1 | 11/2003 | Winterbotham |
| 2004/0073453 | A1 | 4/2004 | Nenov et al. |
| 2004/0172307 | A1 * | 9/2004 | Gruber .................. 705/3 |
| 2004/0186884 | A1 | 9/2004 | Dutordoir |
| 2004/0220829 | A1 | 11/2004 | Baharav et al. |

OTHER PUBLICATIONS

International Search Report & The Written Opinion of the International Searching Authority, Patent Cooperation Treaty, Application No. PCT/US06/31774, Sep. 24, 2007.

Non-Final Office Action, United States Patent & Trademark Office, U.S. Appl. No. 10/387,041, filed Mar. 10, 2003, Aug. 9, 2007.

Response to Non-Final Office Action, U.S. Appl. No. 10/387,041, filed Mar. 10, 2003, Dec. 10, 2007.

Non-Final Office Action, United States Patent & Trademark Office, U.S. Appl. No. 10/641,982, filed Aug. 15, 2003, Jul. 26, 2007.

Response to Non-Final Office Action, U.S. Appl. No. 10/641,982, filed Aug. 15, 2003, Nov. 21, 2007.

Acuff, Richard D., Fagan, M.D., Ph.D, Lawrence M., Rindfleisch, M.S., Thomas C., Levitt, Benajmin J., Ford, M.D., Paul M., "Lightweight, Mobile E-Mail for Intra-Clinic Communication," Jun. 1997, Stanford University School of Medicine, Section on Medical Informatics, p. 4.

Final Office Action, United States Patent & Trademark Office, U.S. Appl. No. 10/387,041, filed Mar. 10, 2003, Mar. 5, 2008.

Final Office Action, United States Patent & Trademark Office, U.S. Appl. No. 10/641,982, filed Aug. 15, 2003, Mar. 7, 2008.

Schatz, Elizabeth, "Reaching a Doctor by E-Mail," Tuesday, Apr. 15, 2003, Wall Street Journal, p. 4.

Parker-Pope, Tara, "Virtual Second Opinions: When the Web Can be Better Than Seeing a Local Doc," Health Journal.

Website, "The Healthy Email Project," [http://www.msu.edu/~healthy/page/project.html], Copyright 2001 Healthy Email Project, Michigan State University.

Website, "Powerful Technology Enabling Stronger Healthcare Partnerships," [https://www.mydoconline.com/Marketing/index.html], MyDocOnline (TM), tools for modern health care, Copyright 2003 MyDocOnline, Inc. All Rights Reserved.

Website, "Health Plan Benefits, Relay Health (SM) Secure Online Communication for Healthcare," [https://www.relayhealth.com/rh/specific/healthPlans/default.aspx], Copyright 1999-2003 RelayHealth Corporation. All Rights Reserved.

Non-Final Office Action, United States Patent & Trademark Office, U.S. Appl. No. 11/086,118, filed Mar. 21, 2005, Feb. 18, 2009.

US Food and Drug Admin., "Sign up for FDA's Free E-Mail Lists," navigated from www.recalls.gov obtained via http://web.archive.org for the date Mar. 19, 2004, http://web.archive.org/web/20040214031829/www.fda.gov/emaillist.html.

Vitros Immunodiagnostic Products, "Urgent Product Correction/Recall Notification," Oct. 25, 2004.

US Food and Drug Admin, "Patient and Physician Attitudes and Behaviors Associated With DTC Promotion of Prescription Drugs—Summary of FDA Survey Research Results," Nov. 19, 2004, Appendix B.3 2002 Physician Survey.

Response to Non-Final Office Action dated May 28, 2009, U.S. Appl. No. 11/086,118, filed Mar. 21, 2005.

Non-Final Office Action dated Jun. 23, 2009, United States Patent & Trademark Office, U.S. Appl. No. 11/208,144, filed Aug. 19, 2005.

Fotsch et al., "Electronic Personal Health Record System", U.S. Appl. No. 11/085,984, filed Mar. 21, 2005.

Fotsch et al., "Electronic Personal Health Record System", U.S. Appl. No. 11/208,144, filed Aug. 19, 2005.

* cited by examiner

Graphical User Interface (Web page) 300

| | Home | Message Inbox | Education Programs | iHealthRecord | Clinicians | iHealthRecord
Overview
Basic Information
Registration Info
Patient I.D. & Notes
Medications
Conditions/Med History
Allergies
Additional Information
Clinicians
Immunizations
Surgeries/Procedures
Nutrition Support
Specialty Modules
Emergency Contact
Caregiver Info
Employment Info
Insurance
Hospitals
Pharmacies
Legal Documents
Request Eligibility ~301
PREMIUM Services
iHealthCard

Eligibility Request

| | |
|---|---|
| Provider Name | Dr. Jones |
| Payer | Blue Cross |
| Provider ID | 2315578 |
| Policy Group ID | est4y78  — 302 |
| Subscriber ID | WER 234 667 — 303 |
| Date of Service | 1/21/2006 |
| Dependent Code | Self |
| Patient's First Name | Jane |
| Patient's Last Name | Doe |

Dr. Jones Medical Clinic

FIG. 3A

Graphical User Interface
(Web page)
350

| | Home | Message Inbox | Education Programs | iHealthRecord | Clinicians |

Sidebar:
- iHealthRecord
- Overview
- Basic Information
- Registration Info
- Patient I.D. & Notes
- Medications
- Conditions/Med History
- Allergies
- Additional Information
- Clinicians
- Immunizations
- Surgeries/Procedures
- Nutrition Support
- Specialty Modules
- Emergency Contact
- Caregiver Info
- Employment Info
- Insurance
- Hospitals
- Eligibility Response
- Legal Documents
- Access Privileges
- PREMIUM Services
- iHealthCard

Eligibility Response

Payer Information
| | |
|---|---|
| Payer | Blue Cross |
| Payer ID | 98456 |

Patient Information
| | |
|---|---|
| Patient Name | Jan Doe |
| Patient Gender | Female |
| Relationship | Self |
| Provider Name | Dr. Jones |
| Provider Phone | 415.369.9660 |

Subscriber Information
| | |
|---|---|
| Patient Name | Jan Doe |
| Patient Gender | Female |
| Subscriber ID | 8899725 |
| Group Number | 0338246 |

Eligibility Information — 360
| | |
|---|---|
| Eligibility | active |
| Begin Effective Date | 1/1/2006 |
| End Effective Date | 12/31/2006 |
| Insurance Type | HMO |

Copay (InNetwork) — 360a
| | |
|---|---|
| Provider After Hours | $10.00 |
| Provider During Hours | $5.00 |
| Facility Hospital | $0.00 |
| Hospital OP Surgery | $0.00 |
| OP Diagnostic Testing | $0.00 |
| OP Lab | $0.00 |
| OP Xray | $0.00 |
| Emergency Room | $0.00 |

Deductables/Out-Of-Pocket (In Network) — 360b
| | Deductable | Out-Of-Pocket |
|---|---|---|
| Patient | $300 | $3500 |
| Patient YTD | $75 | $425 |

Deductables/Out-Of-Pocket (In Network) — 360c
| | Deductable | Out-Of-Pocket |
|---|---|---|
| Patient | $550 | $5000 |
| Patient YTD | $110 | $700 |

FIG. 3B

Graphical User Interface (Web page) 380

Home | Message Inbox | Education Programs | iHealthRecord | Clinicians

Sidebar:
- iHealthRecord
- Overview
- Basic Information
- Registration Info
- Patient I.D. & Notes
- Medications
- Conditions/Med History
- Allergies
- Additional Information
- Clinicians
- Immunizations
- Surgeries/Procedures
- Nutrition Support
- Specialty Modules
- Emergency Contact
- Caregiver Info
- Employment Info
- Insurance
- Hospitals
- Pharmacies
- Legal Documents
- Request Eligibility
- PREMIUM Services
- iHealthCard

Health Record (Medical Information)

Registration Information — 381
- Patient Name: Jan Doe    DOB: 11/11/1969
- Patient Gender: Female
- Patient Address: 649 Mission Street, SF CA 94105
- Patient Phone: 415.710.2545
- Patient email: jandoe@yahoo.com

Patient Identification — 382
- Race: Caucasian
- Height: 5'3"
- Eye Color: Brown
- Weight: 125lbs
- Blood Type: B
- Marital Status: Married

Medications — 383
- Ibuprofen
  - Condition being treated: Back pain
  - Medication Dose: 600mg tablet
  - Medication Frequency: 4x/day
  - Condition being treated: Back pain
  - Medication Dose: 600mg tablet
  - Medication Frequency: 4x/day

Condition/Medical History — 384
- Back Surgery    4/17/97

Allergies — 385
- Penicillin

Graphical User Interface (Web page) 700

| | Home | Message Inbox | Education Programs | iHealthRecord | Clinicians | iHealthRecord
▸Overview
Basic Information
Registration Info
Patient I.D. & Notes
Medications
Conditions/Med History
Allergies
Additional Information
Clinicians
Immunizations
Surgeries/Procedures
Nutrition Support
Specialty Modules
Emergency Contact
Caregiver Info
Employment Info
Insurance
Hospitals
Pharmacies
Legal Documents
Access Privileges
PREMIUM Services
iHealthCard

701 iHealthRecord Overview

Print/View  Full Record / Wallet Card / iHealthRegistration
[?] Help

⚠ The completion of this iHealthRecord does not mean that your clinician will see it. Be sure to directly communicate (in person, via phone, etc.) with your clinicians regarding any significant changes in your health.

Below is a summary of the iHealthRecord Information for jenna 109.
LAST MODIFIED: November 7, 2005

This information can be updated or printed at any time. To go through the iHealthRecord page by page, click Start below.
To go directly to any section of the iHealthRecord, please click on the section name.

Some things to remember:

- Review and update this information at least every 6 months to keep it current.
- To print a copy of this iHealthRecord, click Print Full Record.
- Print a Wallet Card to keep your important health info with you at all times.
- No more filling out the clipboard! Before your next doctor's appointment, click on iHealthRegistration at the top right corner of this page to generate a printable iHealthRegistration form that you can bring with you to your doctor's office.

– Tell a friend or family member about the iHealthRecord

[ Start ▸ ]

✗ Delete YouriHealthRecord

| Basic Information | Created/Modified Date | Options |
|---|---|---|
| Registration Information | Oct 06, 2005 | Edit |
| Patient Identification and Notes | Oct 06, 2005 | Edit |

Graphical User Interface (Web page) 710 iHealthRecord  🖨 Print/View  Full Record / Wallet Card / iHealthRegistration  [?] Help Below is a preview of the information for your iHealthCard. You can use the checkboxes on the right to add/change the information that you would like to be printed on your personalized iHealthCard. If you change any information, use the Save and Preview button to see your changes. When you are finished, click the Order iHealthCard button to send your card to the printer.

712 — Current iHealthRecord: 713
[Save and Preview] [Order iHealthCard] Back to Overview iHealthRecord Preview: 723b

```
[📁] iHealth Card        Logo 711
Angela White
Female DOB:11/11/1969 Height:5'4" Eyes:Brown Hair:Blonde
(415)555-1212 angel69@yahoo.com
iHealthRecord Access: www.bluestein.yourmd.com (ID: Angel69)
Emergency Contact:
Sarah Williams (202)555-2222 (202)555-3333
John White (310)555-4444
My Doctors:
Jane Bluestein, MD (415)555-5555
Kathy Simpson, MD (415)555-0788
```

```
[⚕]
Medications:                  Insurer: Blue Cross CA
Albuterol—use as needed       Subscriber: Angela White
Lipitor—taken daily           DOB: 11/11/1969
Conditions                    Member ID: BC101010102
Asthma
Hypertension                  Insurer: Health Net
Migraine headaches            Subscriber: John White
Allergies                     DOB: 10/05/1970
Dust, Peanut Butter, Penicillin  |||||||||||||
```
723a Note: The final layout of your iHealthCard may not look exactly the same as above.

>> Enter your coupon code [Marquetteihr2005]

Emergency Contact (Pick a maximum of 2 emergency contacts)
- ☑ Sarah Williams — 714
- ☑ John White — 715

Clinicians (Pick a maximum of 2 clinicians)
- ☐ Linda Adams
- ☑ Jane Bluestein
- ☐ Michael Chang
- ☐ Patrick Johnson
- ☑ Kathy Simpson
- ☐ John Smith — 716

Medications
Select a combined total of 10 meds, conditions, and allergies.
- ☑ Albuterol
- ☐ Aspirin
- ☑ Lipitor
- ☐ Multivitamins — 717

Conditions
Select a combined total of 10 meds, conditions, and allergies.
- ☐ Arthritis
- ☑ Asthma
- ☑ Hypertension
- ☑ Migraine headaches — 718

Allergies
Select a combined total of 10 meds, conditions, and allergies.
- ☑ Dust
- ☑ Peanut Butter
- ☑ Penicillin — 719

Insurance (Pick a maximum of 2 insurance plans)
- ☑ Blue Cross CA
- ☑ Health Net

[Save and Preview] [Order iHealthCard] — 720

FIG. 7B

Graphical User Interface
(Web page)
730

| | Home | Message Inbox | Education Programs | iHealthRecord | Clinicians |

| iHealthRecord | |
|---|---|
| Overview | |
| Basic Information | |
| Registration Info | |
| Patient I.D. & Notes | |
| Medications | |
| Conditions/Med History | |
| Allergies | |
| Additional Information | |
| Clinicians | |
| Immunizations | |
| Surgeries/Procedures | |
| Nutrition Support | |
| Specialty Modules | |
| Emergency Contact | |
| Caregiver Info | |
| Employment Info | |
| Insurance | |
| Hospitals | |
| Pharmacies | |
| Legal Documents | |
| Access Privileges | |
| PREMIUM Services | |
| iHealthCard | |

Order Your iHealthRecord Now!    🖨 Print/View  Full Record / Wallet Card / iHealthRegistration   [?] Help Congratulations!

Your coupon code has been validated and your iHealthCards will be printed shortly. They'll be ready for pick-up according the instructions that you have received earlier.

[ Continue ▸ ]

If Patient has a valid Coupon code and card is underwritten, no payment required.

FIG. 7C

Graphical User Interface (Web page) 740

Home | Message Inbox | Education Programs | iHealthRecord | Clinicians

| iHealthRecord |
|---|
| Overview |
| Basic Information |
| Registration Info |
| Patient I.D. & Notes |
| Medications |
| Conditions/Med History |
| Allergies |
| Additional Information |
| Clinicians |
| Immunizations |
| Surgeries/Procedures |
| Nutrition Support |
| Specialty Modules |
| Emergency Contact |
| Caregiver Info |
| Employment Info |
| Insurance |
| Hospitals |
| Pharmacies |
| Legal Documents |
| Access Privileges |
| PREMIUM Services |
| iHealthCard |

Order Your iHealthCards Now!

Print/View  Full Record / Wallet Card / iHealthRegistration
[?] Help

I'm ready to order my iHealthCards.

○ I would like to order 2 iHealthCards for $20
○ I would like to order 4 iHealthCards for $40

Billing Information (You must enter the information below exactly as it appears on your credit card statement)

Name On Card: [         ]

☐ Check box if billing address is the same as shipping address

Billing Address 1 [         ]
Billing Address 2 [         ]
City [         ]
Billing State/Province [         ]
Billing Zip/Postal Code [    ]
Card Type: [Visa ▼]
Card Number: [         ]
Card Expiration: [1 ▼] / [2005 ▼]

[Continue ▶]

If patient does not have a Coupon code, collect payment and shipping information.

FIG. 7D

METHOD, SYSTEM AND ARTICLE OF MANUFACTURE, SUCH AS A CARD, TO PROVIDE USER SELECTABLE MEDICAL INFORMATION AND INFORMATION TO OBTAIN ELIGIBILITY OF HEALTHCARE PAYMENTS

RELATED APPLICATIONS

The present application is a continuation-in-part of U.S. patent application Ser. No. 11/208,144 filed Aug. 19, 2005 entitled "ELECTRONIC PERSONAL HEALTH RECORD SYSTEM," which is a continuation-in-part of application Ser. No. 11/085,984 filed Mar. 21, 2005 entitled "ELECTRONIC PERSONAL HEALTH RECORD SYSTEM," which is a continuation-in-part of application Ser. No. 10/387,041 filed on Mar. 10, 2003 now abandoned entitled "HEALTHCARE PROVIDER-PATIENT ONLINE CONSULTATION SYSTEM," and is a continuation-in-part of application Ser. No. 10/641,982 filed on Aug. 15, 2003 now abandoned entitled "HEALTHCARE PROVIDER-PATIENT ONLINE CONSULTATION AND COMPLIANCE PROGRAM."

FIELD OF THE INVENTION

This invention relates generally to providing medical information, such as medical history of an individual, and eligibility for payment of healthcare.

BACKGROUND

A healthcare provider may have difficulty in obtaining medical information desired for a healthcare recipient, such as a patient. The medical information, such as an allergy or an image of a healthcare recipient, may be necessary for a proper diagnosis and/or treatment. Medical information of the healthcare recipient may be distributed in a variety of locations and in a variety of different formats. Medical information may be stored, for example, at a previous healthcare provider, a specialist, a healthcare plan provider (such as insurance company) or the healthcare recipient (or caregiver). Medical information may be stored in either an electronic or paper format. Medical information possessed by different healthcare providers (or the healthcare recipient) may have incompatible electronic formats that prevent one healthcare provider from readily accessing transferred medical information. One healthcare provider may use particular application software for retrieving, creating and viewing images, while another healthcare provider uses different application software for retrieving, creating and viewing images. Medical information also may be incomplete or lost during storage and transfers that may lead to duplicate tests, unnecessary hospitalizations and other side effects contributing to healthcare costs. A request for transferring medical information may also increase healthcare costs. The delay in waiting for the transferred medical information may also lead to a delay in diagnosis or treatment that reduces the effectiveness of the healthcare.

A healthcare provider also may have difficulty in obtaining information regarding eligibility of healthcare payments, such as whether a patient is covered by a particular insurance healthcare plan or insurance carrier. A healthcare recipient may have a document that indicates coverage of a particular healthcare plan, such as a policy number. Typically, a healthcare recipient does not select what information and in what form the information is provided on the document. A healthcare recipient may provide this document to the healthcare provider before diagnosis or treatment. However, this document may not provide current and detailed eligibility information, such as whether a particular test is authorized or whether the healthcare recipient is currently eligible. For example, the healthcare recipient may have changed employment and thus insurance healthcare plans are not reflected by the document or alternatively has reached insurance coverage limits.

BRIEF DESCRIPTION OF THE FIGURES

FIG. 3A illustrates a graphical user interface, such as a Web page, to provide a request for eligibility information according to an embodiment.

FIG. 3B illustrates a graphical user interface, such as a Web page, to provide a response to a request for eligibility according to an embodiment.

FIG. 3C illustrates a graphical user interface, such as a Web page, to provide medical information, such as a health record, according to an embodiment.

FIGS. 7A-D illustrate a graphical user interface, such as a Web page, to provide a customized card according to an embodiment.

DETAILED DESCRIPTION

Figure 1:
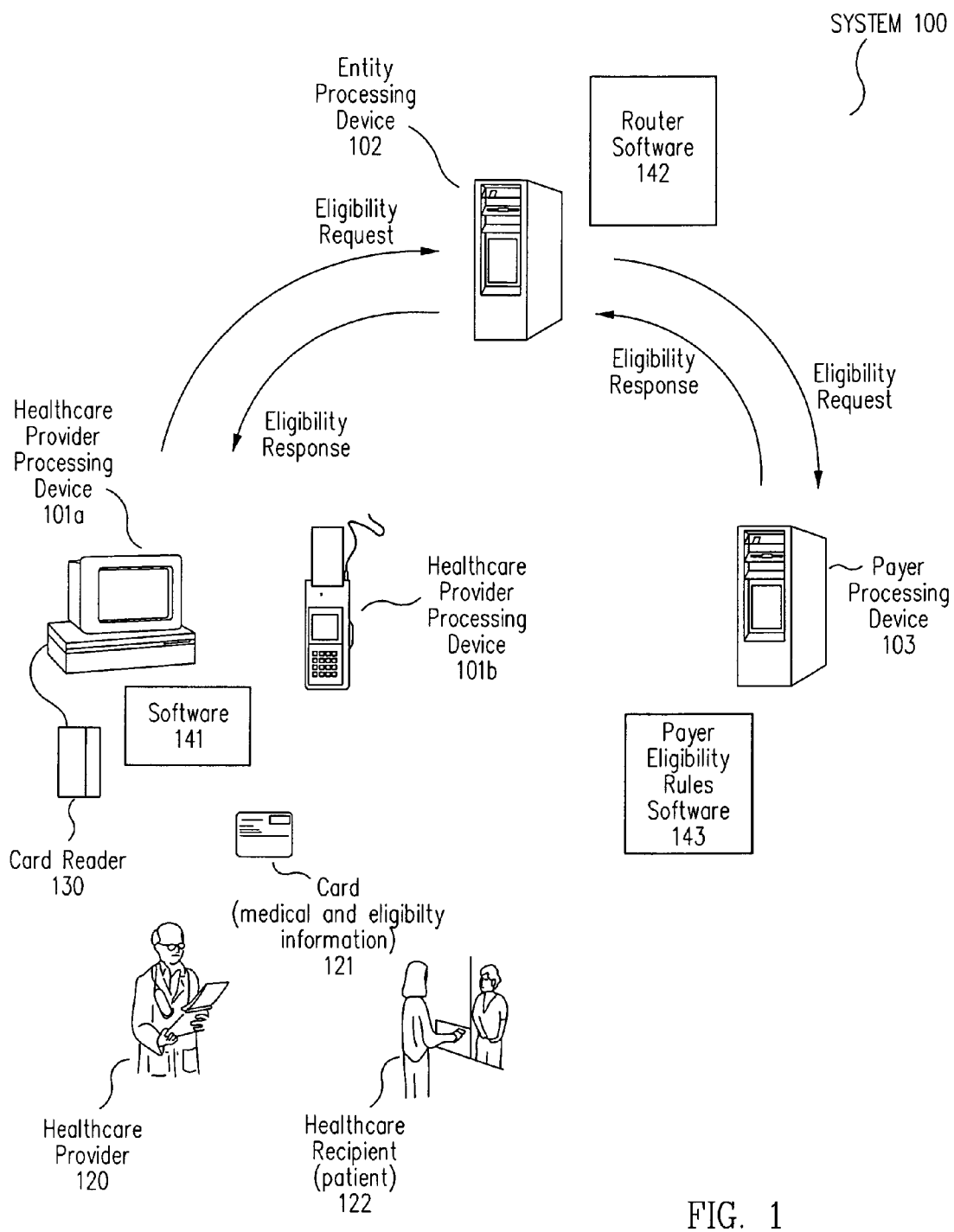
FIG. 1 illustrates a system using a card having medical information and/or information to obtain eligibility of healthcare payments according to an embodiment.

An article of manufacture, such as a credit card sized health card having a magnetic strip, includes user selected medical information and/or information to obtain eligibility of healthcare payments and/or information to access remotely stored medical information, such as a personal health record, in embodiments. Information to access remotely stored medical information of an individual and/or information to obtain eligibility of healthcare payments of that individual is magnetically stored on the magnetic strip. An individual, such as a healthcare recipient (or caregiver of the healthcare recipient), or sponsor may customize the medical information displayed on the health card. In an embodiment, a method obtains and stores medical information including a medical history in a machine-readable format, such as an electronic format, at a remote site. An interface to select a portion of the medical information is provided to an individual or user. In response to a user selection, the portion of the medical information is displayed on a substrate, such as a health card, and the medical information may be accessed from the remote site by using information recorded in a machine-readable format, such as on a magnetic strip, that is disposed on the health card. In embodiments, the portion of medical information displayed on the health card may be emergency contact information and/or allergies. The remotely stored medical information may be accessed by reading an address indicating where the medical information is stored, such as a universal resource locator (URL), a user identifier and a user password stored on the magnetic strip. The health card is then provided to the user.

In an embodiment, a system includes a healthcare provider processing device to obtain information to access eligibility information from the health card and generating an eligibility request to an entity processing device that forwards the eligibility request to a payer processing device. An eligibility response from the payer processing device is then provided to the healthcare provider processing device via the entity processing device.

In an embodiment, medical information in a paper format is provided and converted into a machine-readable format. The medical information in a machine-readable format is then sorted and stored by respective medical categories.

Thus, a healthcare provider is able to obtain timely, complete, and current medical information of a healthcare recipient as well as detailed eligibility information regarding payment of healthcare for the healthcare recipient before providing healthcare. A user is able to select what medical information is displayed or viewable by individuals and what medical information is viewable by a machine or processing device. The effect of medical treatment and/or diagnosis may be improved because delays in obtaining medical and eligibility information are reduced. Urgent care may be provided in a timely manner because of immediate access to complete medical information and emergency contact information. Likewise, eliminating duplicate tests, unnecessary hospitalization, side effects and requests for medical information may reduce the cost of providing healthcare.

FIG. 1 illustrates a system 100 using a card 121 having medical information and/or information to obtain eligibility of healthcare payments according to an embodiment. System 100 includes a healthcare provider processing device 101a or alternatively processing device 101b (101a/b), entity processing device 102 and payer processing device 103. In an embodiment, processing device 101a is a general-purpose computer coupled to a wedge 130. In an embodiment, processing device 101b is a point-of-care eligibility device or a card reader. In an embodiment, processing devices 101a/b, 102 and 103 are coupled by a network (wired and/or wireless) that may include a wide area network, local area network, telephone lines, and the Internet (also known as the World Wide Web), singly or in combination. In embodiments, system 100 includes a plurality of processing devices 101a/b and a plurality of processing devices 103. In an embodiment, healthcare processing device 101a is coupled via the Internet to a third party processing device, such as processing device 902 shown in FIG. 9, that stores medical information of healthcare recipient 122 (as well as others) in a machine (computer) readable or electronic format.

In an embodiment, a healthcare recipient 122 provides card 121 that stores an address to obtain remotely stored machine readable medical information, a user (or individual) identifier and password and/or information to obtain eligibility of healthcare payments to healthcare provider 120. Healthcare provider 120 then uses card 121 with processing device 101a/b to obtain medical information of healthcare recipient 122 (from processing device 902 in an embodiment) and/or generate an eligibility request for payment of healthcare (to payer processing device 103 via entity processing device 102).

In an embodiment, healthcare provider 120 uses card 121 with processing device 101a and a wedge 130 to obtain information to access medical information and/or information to obtain eligibility of healthcare payments by swiping card 121 through wedge 130. In an embodiment, wedge 130 is used to obtain information for accessing medical information and/or information to obtain eligibility of healthcare payments stored on a magnetic strip disposed on card 121. In an embodiment, processing device 101a includes a processor coupled to a machine-readable medium (such as a storage device including an integrated circuit memory device) that stores an application software 141 (machine readable/executable instructions) to read a URL, user identifier and password from card 121 via wedge 130 and access remotely stored medical information of the healthcare recipient. In an embodiment, application software 141 accesses a browser stored on processing device 101a.

In an alternate embodiment, healthcare provider 120 uses card 121 with processing device 101b to obtain eligibility information by swiping card 121 through processing device 101b. In an embodiment, processing device 101b stores an application software 141 (machine readable/executable instructions) to read information to obtain eligibility information from card 121. Processing device 101a/b generates an eligibility request to processing device 102 in response to information used to obtain eligibility information obtained from card 121. Processing device 102 then routes or forwards the eligibility request to processing device 103. In an embodiment, processing device 102 stores router software 142 (machine readable/executable instructions) to route the eligibility request to the appropriate payer processing device. In an embodiment, router software 142 includes a plurality of addresses to a plurality of processing devices 103 (or Web sites) that are used to route the eligibility request in response to the information to obtain eligibility information, such as a payer identifier (read from card 121), in the eligibility request. Router software 142 also keeps track of the source address (or processing device 101a/b address) of the eligibility request so that a subsequent eligibility response from the payer processing device 103 may be forwarded to processing device 101a/b.

Payer processing device 103 generates an eligibility response to entity processing device 102 in response to the eligibility request from entity processing device 102. In an embodiment, processing device 102 stores payer eligibility rules software 143 (machine readable/executable instructions) to decide the eligibility information of healthcare recipient 122 at a particular time. Payer eligibility rules software 143 determines whether healthcare recipient 122 is a member of a particular healthcare plan and detailed eligibility information, such as eligibility of payment, eligibility of particular treatments and/or benefits, percent coinsurance, co-pay amount, deductible and/or limit of benefits (and/or current amount of benefits used during a period of time, such as year to date (YTD)). In an embodiment, payer eligibility rules software 143 generates the eligibility response.

Figure 9:
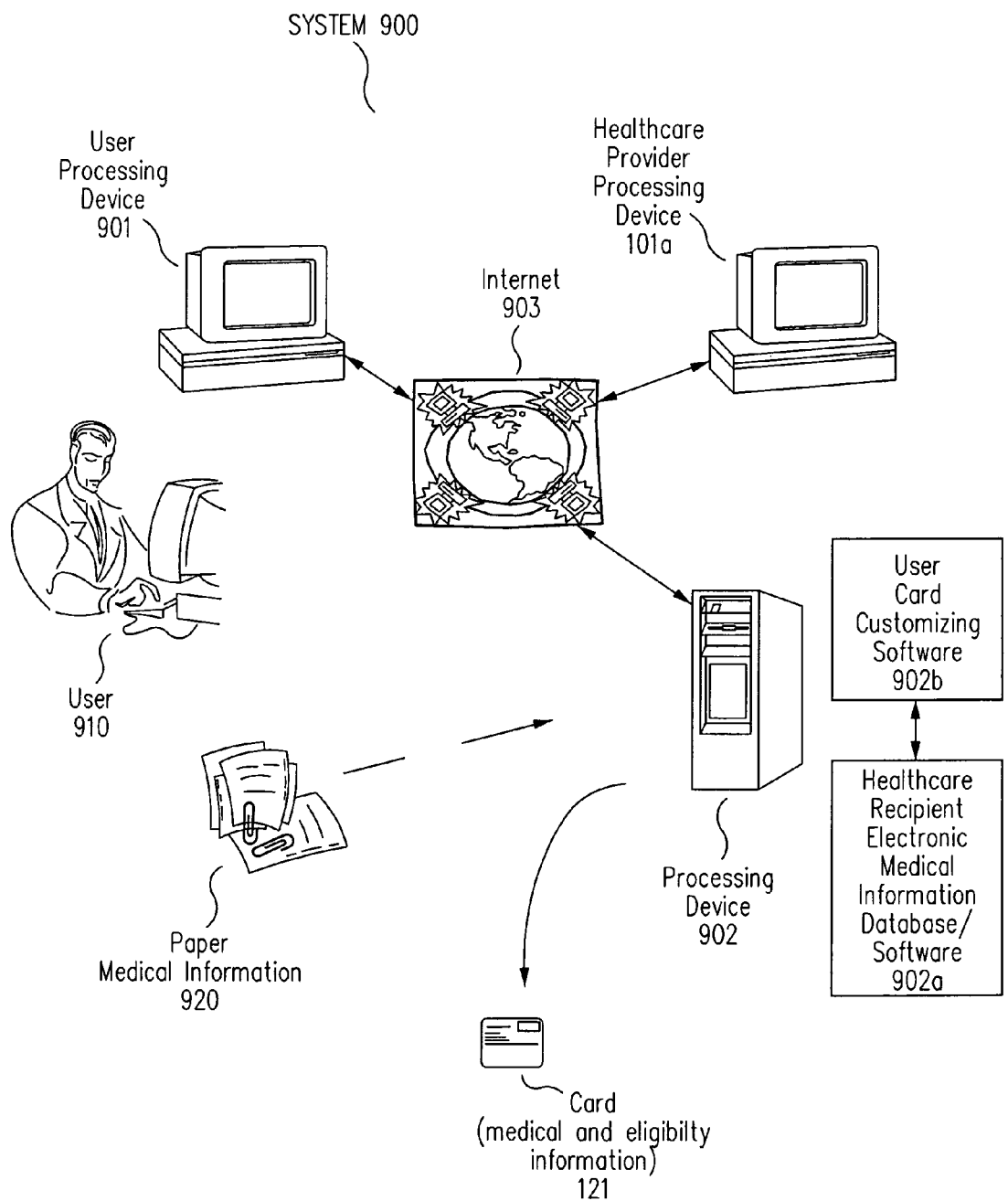
FIG. 9 illustrates a system for converting paper medical information into a categorized electronic format according to an embodiment.

In an embodiment, processing devices 101a, 102 and 103 (also processing device 902 as seen in FIG. 9) shown in FIG. 1 are at least a server, a mainframe computer, a general purpose computer or an equivalent thereof. In an embodiment, processing devices 101a, 102, 103 and 902 respectively include at least one processor coupled to a machine-readable medium (such as a storage device including an integrated circuit memory device) for storing software or executable machine-readable instructions. In embodiments, processing devices 101a, 102, 103 and 902 include a distributed architecture or represent many processing devices having respective processors located in near or far physical proximity. In an embodiment, processing device 101a shown in FIG. 1 is an information appliance, a desktop computer, a handheld computer, a telephone, a personal digital assistant (PDA) or an equivalent thereof. In an embodiment, processing devices 101a, 102, 103 and 902 are coupled to the Internet by a wired and/or wireless connection.

In an embodiment, a healthcare provider 120 may be a healthcare provider authorized to practice medicine, such as a physician, nurse, physician's assistant, or nurse practitioner. In embodiments, hospitals, medical groups, universities, health maintenance organizations (HMOs), medical centers, emergency rooms (ER) and/or laboratories employ or are associated with healthcare provider 120. In other embodiments, healthcare provider 120 is a chiropractor, optometrist or dentist. In an embodiment, healthcare provider 120 is a service provider such as pharmacist or lab technician who provides services to primary healthcare providers such as physicians. In an embodiment, healthcare provider 120 is a physician's assistant that does not practice independently. In an embodiment, healthcare provider 120 merely needs to be subservient to a healthcare provider (e.g., physician) and working within the healthcare provider's practice group, where the healthcare provider is associated with the healthcare provider network in an embodiment. In an embodiment, a healthcare provider 120 may be anyone who obtains medical information and/or eligibility information on behalf of a physician in conjunction with care being provided by a physician or other healthcare provider. In an embodiment, healthcare provider 120 may merely be an individual, who works in the healthcare industry, and individual who is merely associated with a physician, or an individual who provides healthcare for the individual.

In an embodiment, healthcare recipient 122 is an individual or a patient of healthcare provider 120. Healthcare recipient 122 may be a relative (e.g., parent or sibling), caregiver or individual covered by another individual's health insurance or healthcare plan in embodiments.

In an embodiment, medical information stored on processing device 109 is in the form of "an electronic personal health record" as described in the above referenced U.S. patent application Ser. No. 11/208,144 filed Aug. 19, 2005 entitled "ELECTRONIC PERSONAL HEALTH RECORD SYSTEM." In an embodiment, medical information may include information that may be pertinent to the medical history of the patient such as medications, conditions, allergies, surgeries, immunizations (all—current and past) family medical history, lifestyle information, health risks (e.g. sexual encounters), vital signs, tests or lab results, imaging results (e.g., x-rays), and a "review of systems" indicating a review of the patient's systems by a healthcare provider 120. Medical information may also include registry information indicating implantable devices or diseases pertinent to healthcare recipient 122. Medical information may include contact information such as emergency contact information, caregiver contact information, and physician information identifying one or more physicians of healthcare recipient 122. Healthcare recipient 122 may also choose to specify his or her preferences, such as at least one preferred pharmacy and/or at least one preferred hospital. Moreover, a photograph of healthcare recipient 122 may also be included with the medical information.

In accordance with one embodiment, a healthcare recipient 122 and/or healthcare provider 120 submits basic information via a registration process as described in the above referenced U.S. patent application Ser. No. 11/208,144 filed Aug. 19, 2005 entitled "ELECTRONIC PERSONAL HEALTH RECORD SYSTEM." In accordance with an alternative embodiment, a healthcare recipient 122 must register through a physician's web site (which may be located on processing device 101a) in order to input or update medical information via the physician's web site. Thus, if the user has not yet registered with the physician's web site, the user may go through the registration process in order to submit his or her medical information via the physician's web site. In an embodiment, a healthcare recipient is not able to register and input medical information unless the healthcare recipient first requests healthcare from a healthcare provider who is currently providing healthcare services to or associated with the healthcare recipient. Thus, a healthcare provider is able to authenticate the healthcare recipient (and the medical information associated with the healthcare recipient) when healthcare services are provided to the healthcare recipient. For example, a healthcare provider will be able to authenticate that Jane Doe is in fact a female having a certain height and weight with particular medical conditions, etc. during Jane Doe's scheduled treatment (or having previously treated her). In an embodiment, a healthcare recipient may not register until the healthcare provider confirms that healthcare services have or will be provided shortly (for example, the healthcare recipient is on a patient list of the physician or scheduled for an appointment). This authentication of a healthcare recipient (patient) or a health record holder provides healthcare providers and third parties such as payers, software vendors—including e-prescribing and other vendors who process patient clinical information—and others with knowledge that a healthcare provider has authenticated a patient, which will mitigate concerns over patient authenticity and allow them to transfer medical information to the health record holder for inclusion in to their health record. In accordance with one embodiment, the user may click on the "Log In" hypertext link to log in or the "New User" hypertext link in order to register with the physician's web site as a new user.

Figure 2:
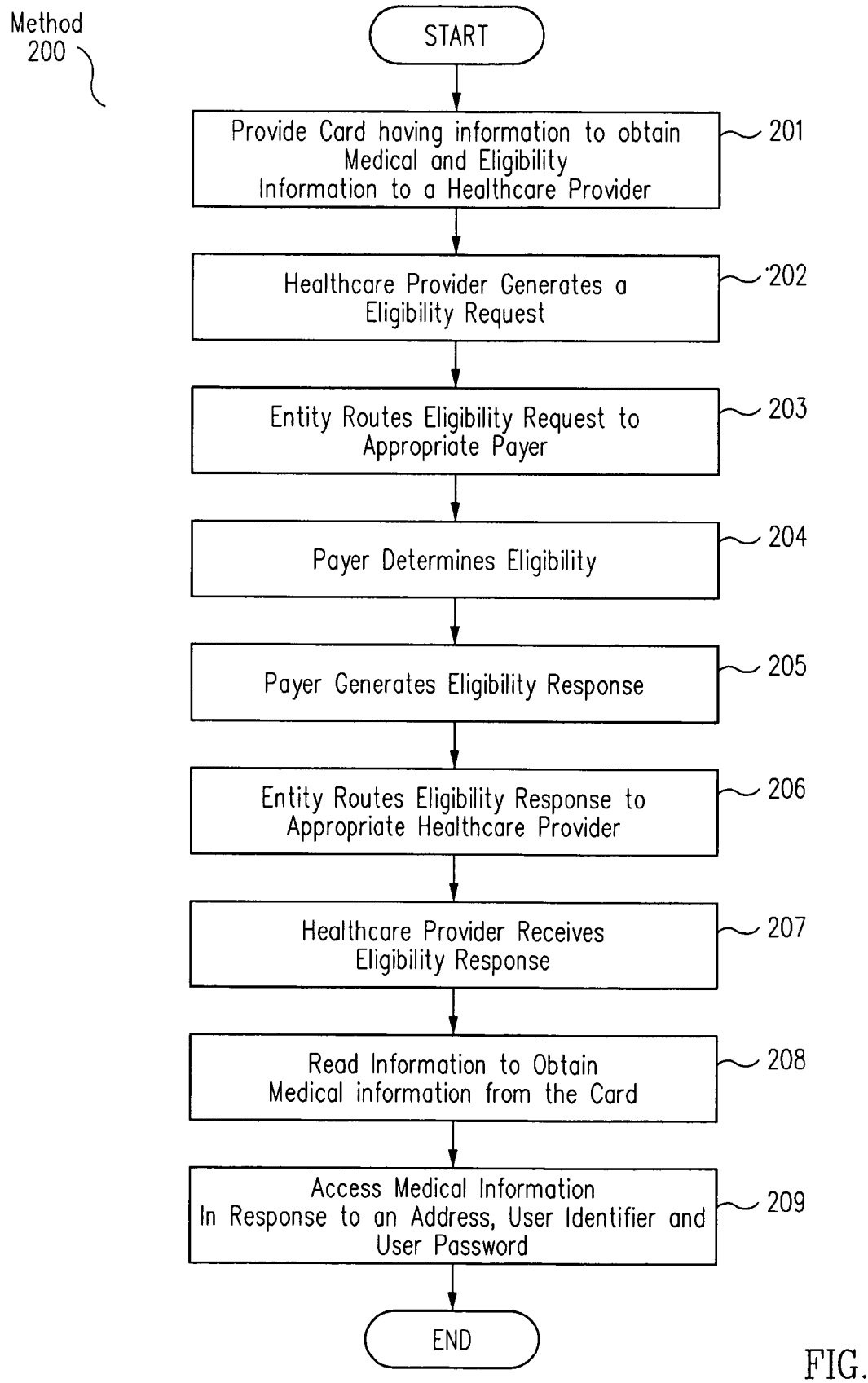
FIG. 2 illustrates a method using a card having medical information and/or information to obtain eligibility of healthcare payments according to an embodiment.
Figure 6:
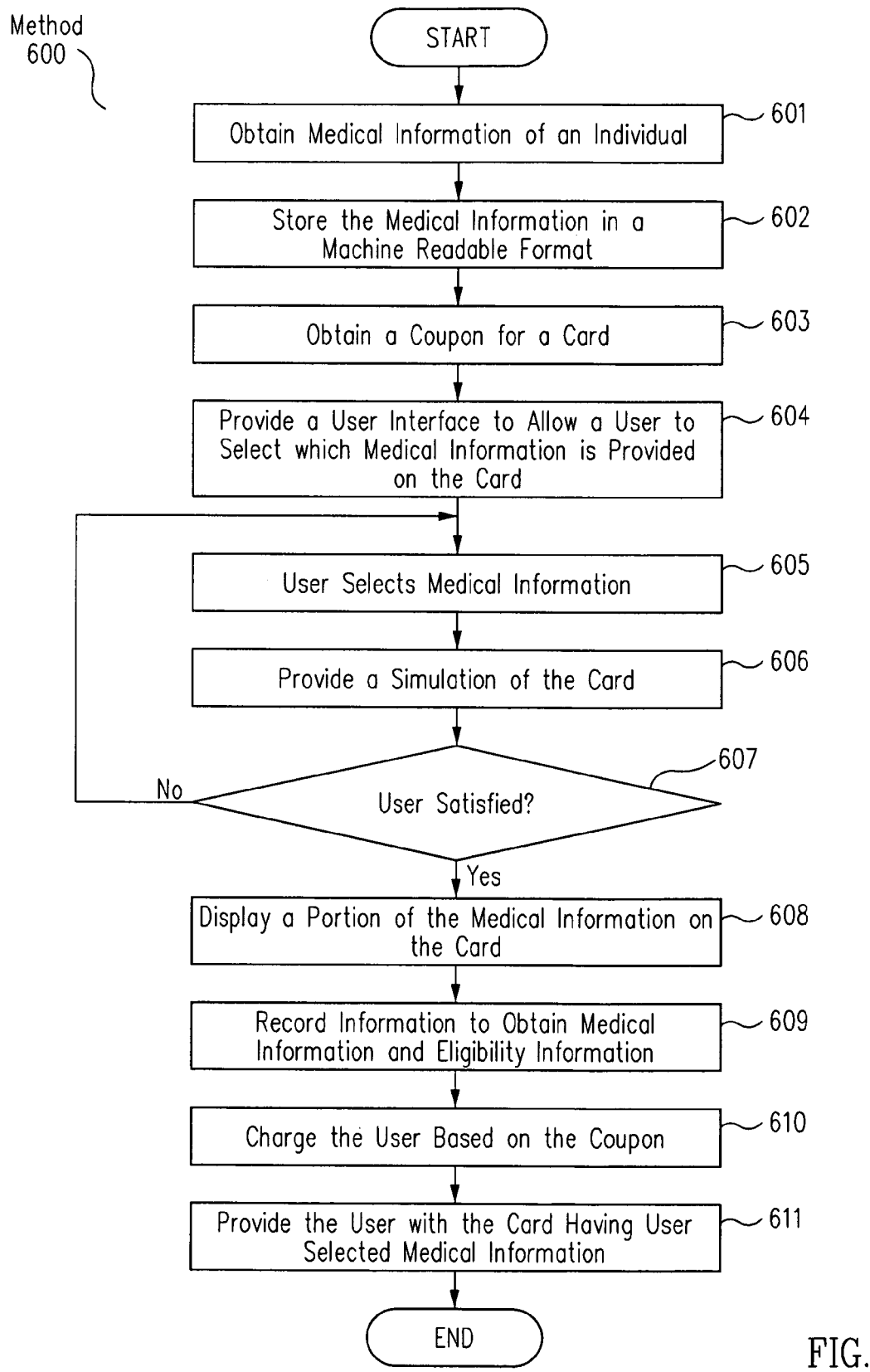
FIG. 6 illustrates a method to allow a user to customize a card having medical information and/or information to obtain eligibility of healthcare payments according to an embodiment.
Figure 10:
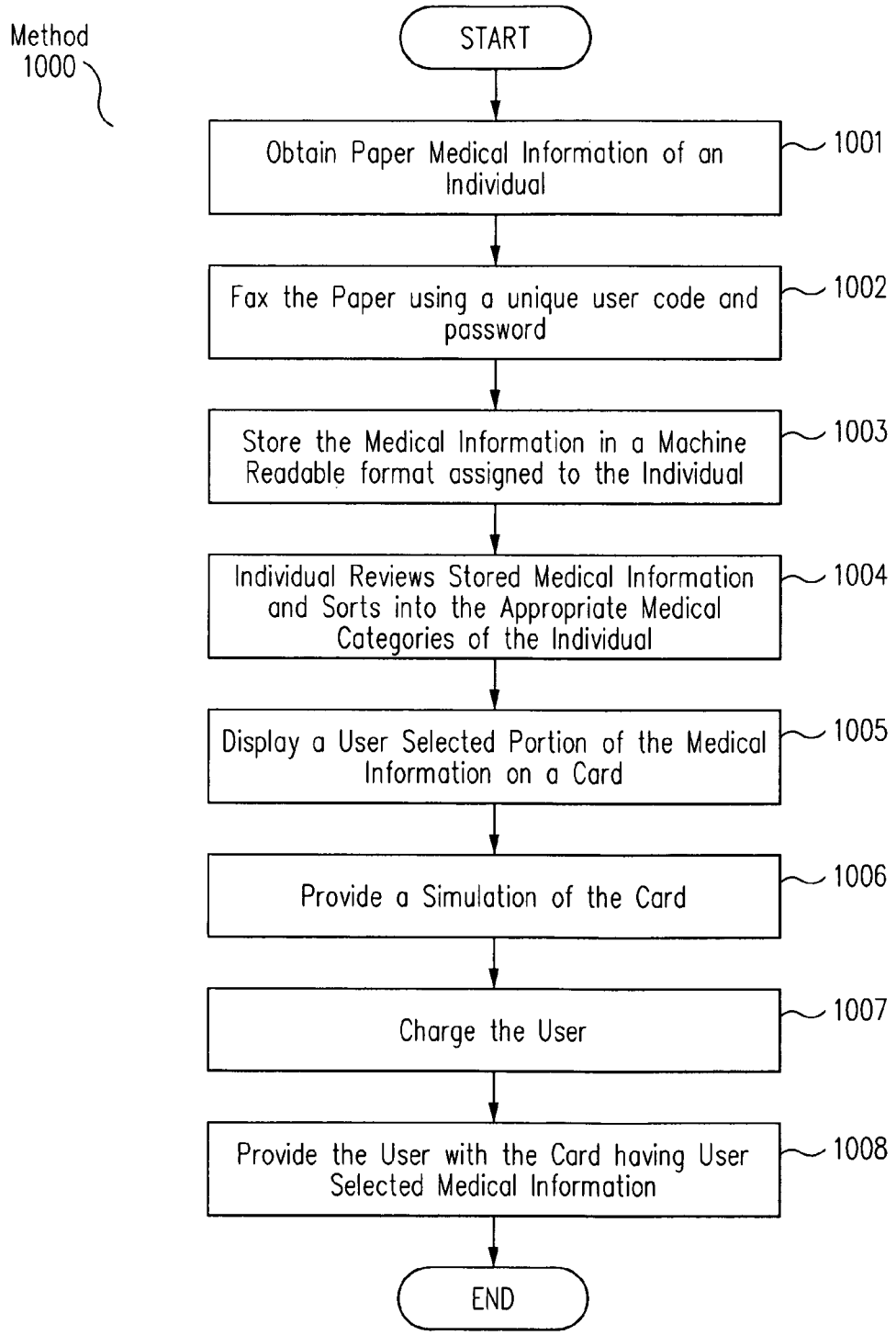
FIG. 10 illustrates a method for converting paper medical information into a categorized electronic format according to an embodiment.

FIG. 2 illustrates a method 200 using a card 121 having information to access remotely stored medical information and/or information to obtain eligibility of healthcare payments according to embodiments. FIG. 2, as well as FIGS. 6 and 10, illustrate logic boxes or steps representing the performance of specific functions. In alternate embodiments, more or fewer logic boxes or steps are used. In an embodiment, a logic box or step may represent, at least in part, an execution of software. Software may be a software program, a software object, a software function, a software subroutine, a software method, a software instance, one or more machine readable/executable instructions, a code fragment or a database. In an embodiment, a logic box or step may represent, at least in part, a hardware operation or an individual operation, such as healthcare provider 120 and healthcare recipient 122, singly or in combination.

Method 200 begins by providing a card having information to obtain medical information and/or information to obtain eligibility of healthcare payments to a healthcare provider as illustrated in logic block 201. In an embodiment, healthcare recipient 122 provides card 121 to healthcare provider 120 as illustrated in FIG. 1. As described herein, card 121 displays user selectable medical information and information to obtain remotely stored medical information and eligibility of healthcare payments regarding healthcare recipient 122.

In logic block 202, a healthcare provider processing device generates an eligibility request regarding payment of healthcare to a payer processing device (via an entity processing device). In a web-based embodiment, processing device 101a generates the eligibility request after a healthcare provider 120 swipes card 121 through wedge 130. In the web-based embodiment, processing device 101a is a general purpose processing device, such as a desktop computer. In a web-based embodiment, healthcare provider 120 is provided with a graphic user interface, such as Web page 300, to a display of processing device 101a as shown in FIG. 3A in response to information obtained from card 121 and application software 141 that executes on processing device 101a.

In a web-based embodiment, information is transferred between processing devices, by way of the Internet 903 shown in FIG. 9, using numerous type of technologies. For example, individual processing device 101a accomplishes information transactions with processing devices 102 and 902 by using the Hypertext Transfer Protocol ("HTTP"). Healthcare provider 120 accesses, by way of individual processing device 101a, Web pages or documents on the Web (that may include text, graphics, images, sound and/or video) stored on Internet 903 or processing device 902 using typically a standard page description language known as the Hypertext Markup Language ("HTML"). HTML provides basic document or Web page formatting and allows for "links" to other Web pages that may be stored on other processing devices. A URL having a specific syntax identifies a network path or connection to a Web page stored on a processing device or in Internet 903. Embedded hypertext links on a particular Web page can be used to find related information. By clicking on a hypertext link in a particular Web page, healthcare provider 120 can display another related Web page or even invoke a related software program.

In a Web-based embodiment, retrieval of information is generally achieved by the use of an HTML-compatible "browser" (for example, Microsoft® Explorer) stored on processing device 101a. When healthcare provider 120 using a browser specifies a link via a URL, processing device 101a issues a request to a naming service to map a hostname in the URL to a particular network Internet Protocol (IP) address at which the processing device, such as processing device 902 is located. The naming service returns a list of one or more IP addresses that can respond to the request. Using one of the IP addresses, a browser establishes a connection to a server. If the server is available, it returns a Web page or other object formatted according to HTML.

A Web site is a set of interconnected Web pages, usually including a homepage, generally located on the same server, and prepared and maintained as a collection of information by a person, group or organization.

In an embodiment, a graphical user interface, such as Web page 300, is provided to healthcare provider 120 in response to wedge 130 reading a URL from a magnetic strip of card 121. In an embodiment, software 902a stored on processing device 902 provides Web page 300. Other healthcare recipient information stored on the magnetic strip is provided into fields of Web page 300. As can be seen, the names of the healthcare provider and payer or "Dr. Jones" and "Blue Cross," respectively are displayed on Web page 300 as well the (healthcare) provider (identifier) ID—"2315578". Policy Group ID and subscriber ID values or numbers are read from card 121 and provided in the fields 302 and 303 of page 300. After further information may be provided to page 300, healthcare provider 120 may generate an eligibility request by selecting or clicking on (via a mouse or other pointing device coupled to processing device 101a) the simulated button labeled "Request Eligibility" 301. As illustrated by logic block 207 in FIG. 2 and graphic user interface (or Web page 350) of FIG. 3B, eligibility information is then provided to healthcare provider 120 after a payer processing device receives the eligibility request. In an embodiment, Web page 350 includes eligibility information 360, such as copay (in network) information 360a for particular services or treatments (for example, x-rays), deductibles/out-of-pocket (in network) information 360b and deductibles/out-of-pocket (out of network) information 360c. In an embodiment, Web page 350 is provided to a display of processing device 101a and may be saved and/or printed. In an embodiment, Web page 350 also includes payer information, patient information and subscriber information. A payer associated with payer processing device 103 may be an insurance company, HMO, health plan provider/administrator, trade association, government agency, non-profit organization or other business entity responsible for paying healthcare.

Figure 4:
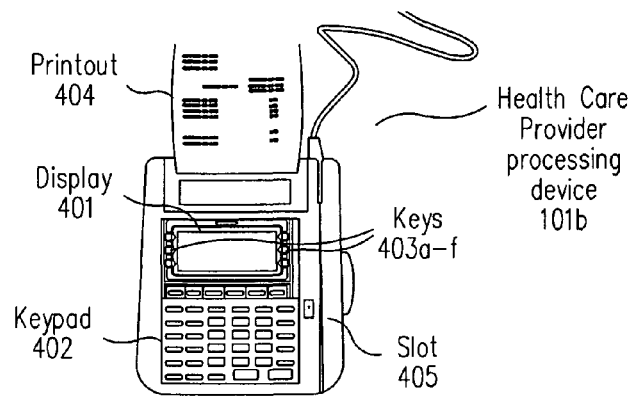
FIG. 4 illustrates a processing device for obtaining eligibility information according to an embodiment.

In an alternate point-of-care device embodiment, processing device 101b is used with card 121 to generate an eligibility request in logic block 202. Processing device 101b is shown in FIG. 4 while operation of processing device 101b is shown in FIGS. 5A-F. Processing device 101b includes display 401, printout 404 (provided by a printer), keypad 402, slot 405 (or card reader) and keys 403a-f. In a point-of-care processing device embodiment, processing device 101b generates the eligibility request after a healthcare provider 120 swipes card 121 through slot 405.

Figure 5A:
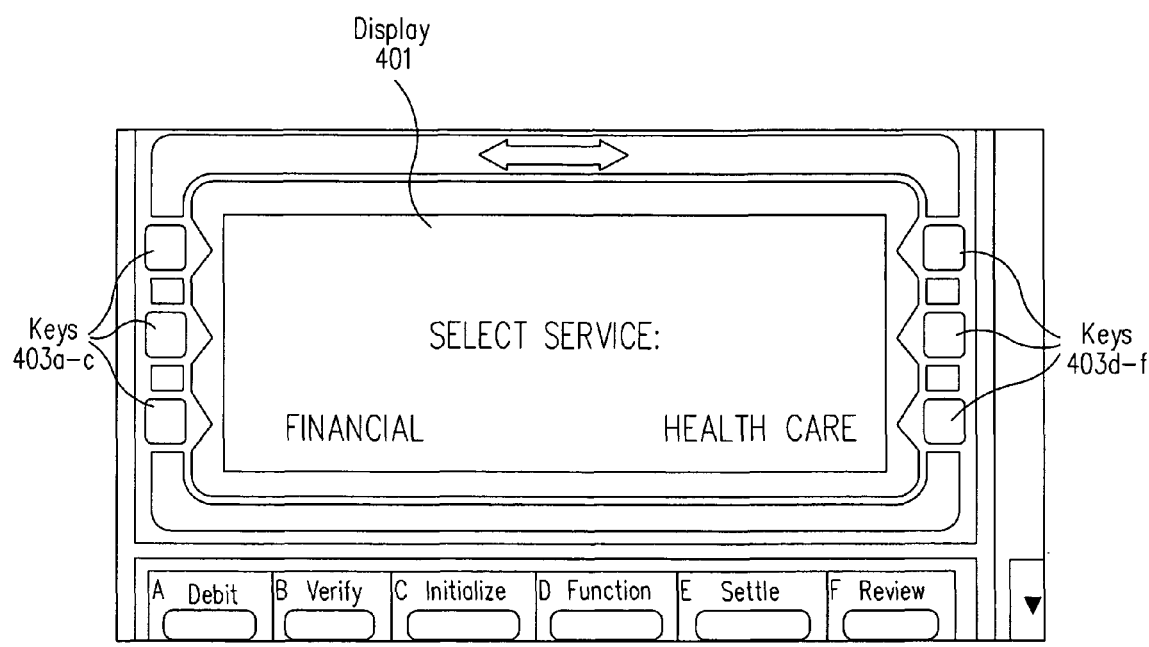
FIGS. 5A-F illustrate graphical user interfaces, such as information displayed on the processing device shown in FIG. 4 according to an embodiment.
Figure 5B:
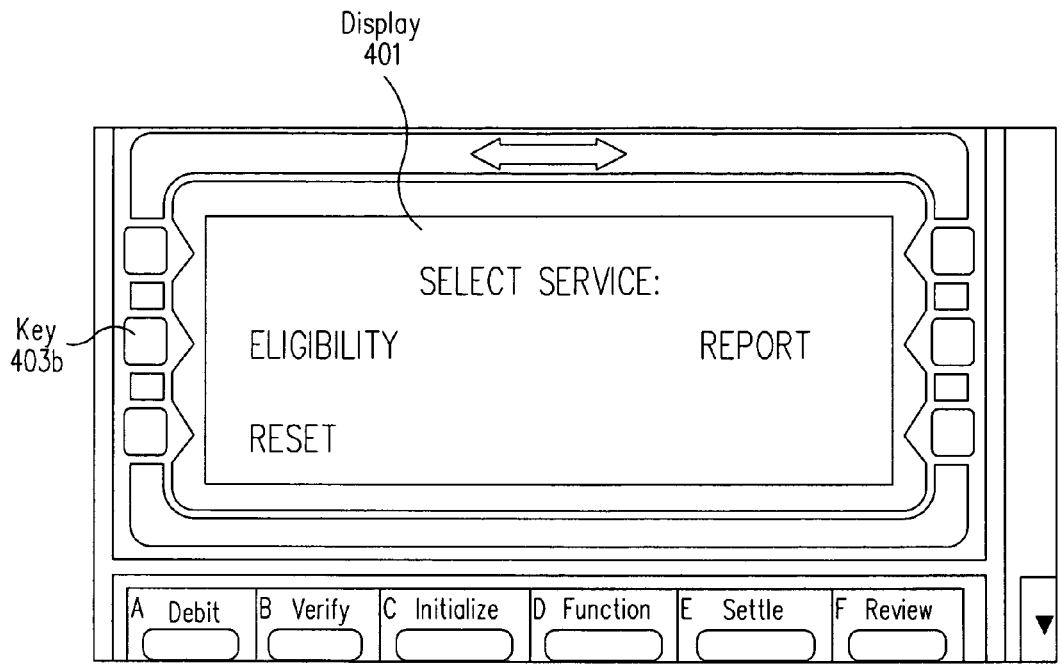
Figure 5C:
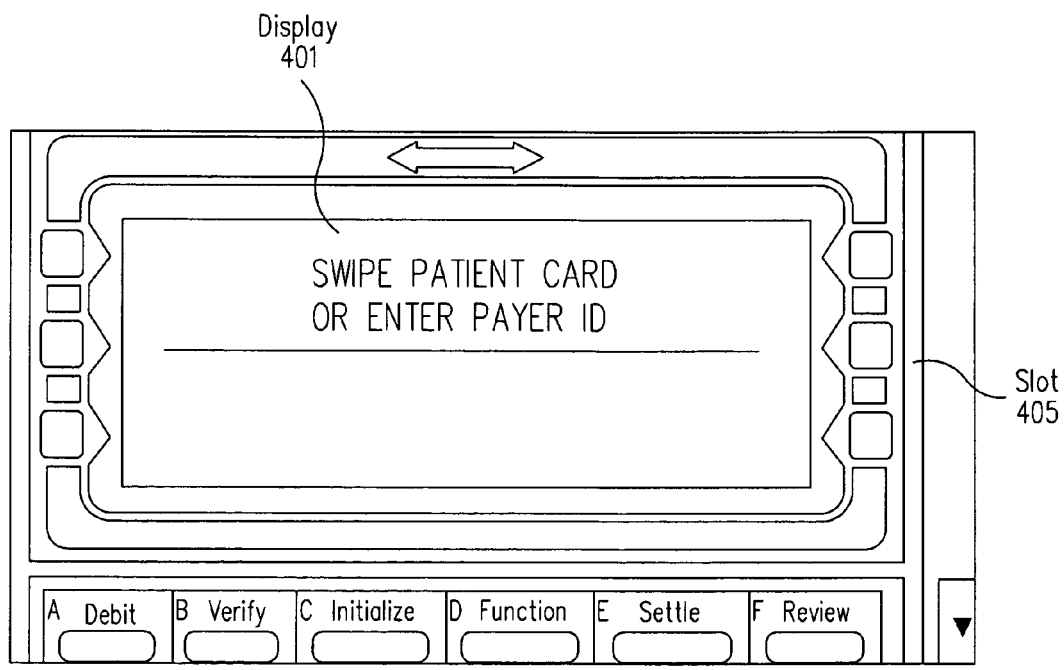
Figure 5D:
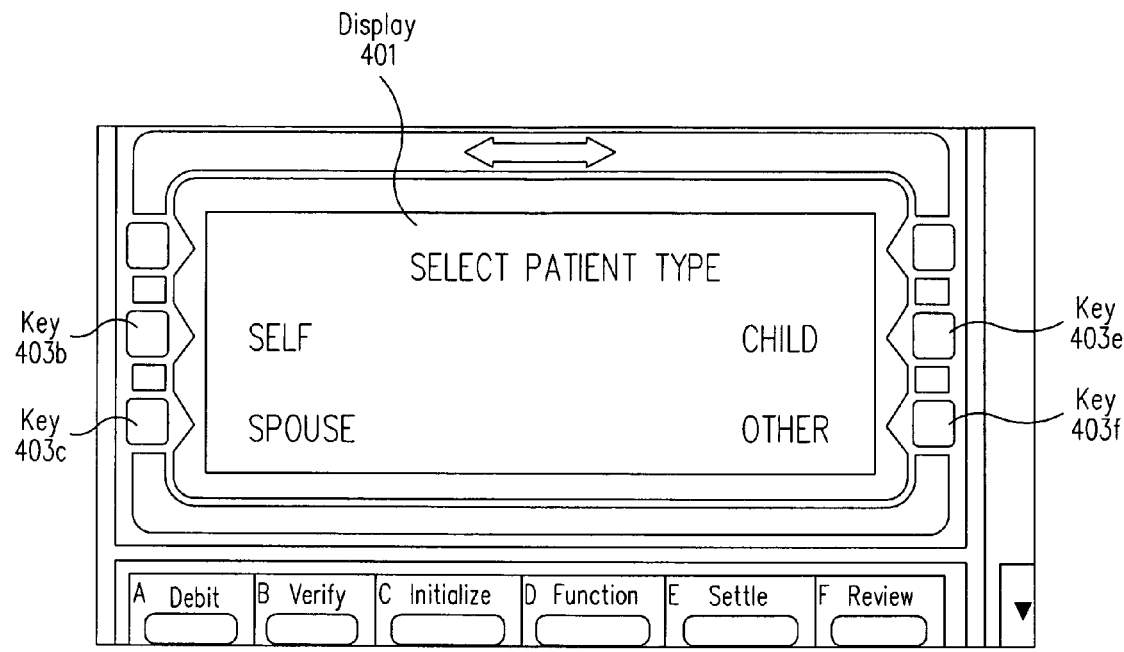
Figure 5E:
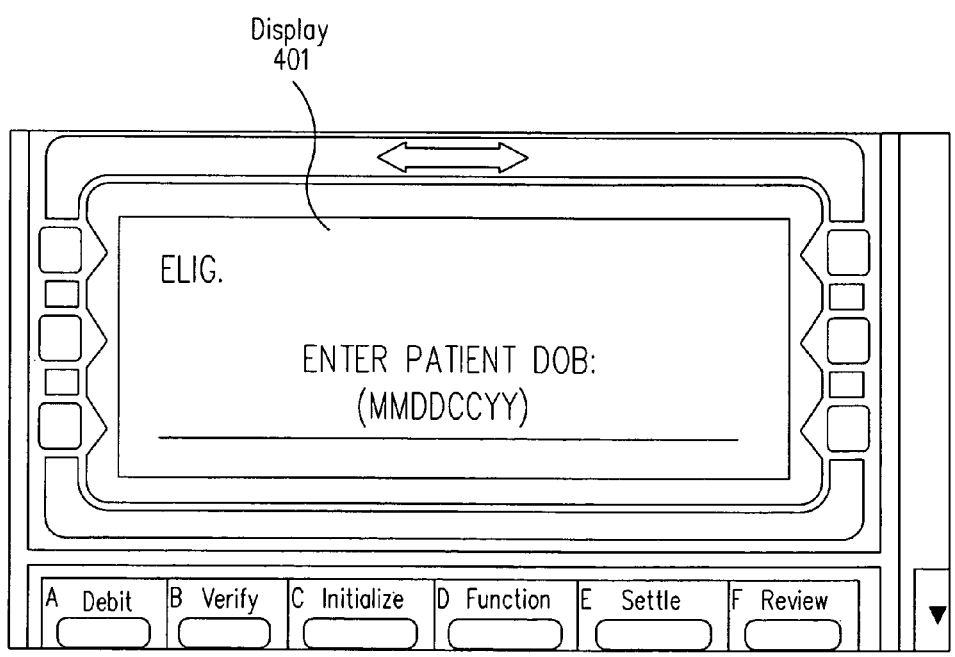
Figure 5F:
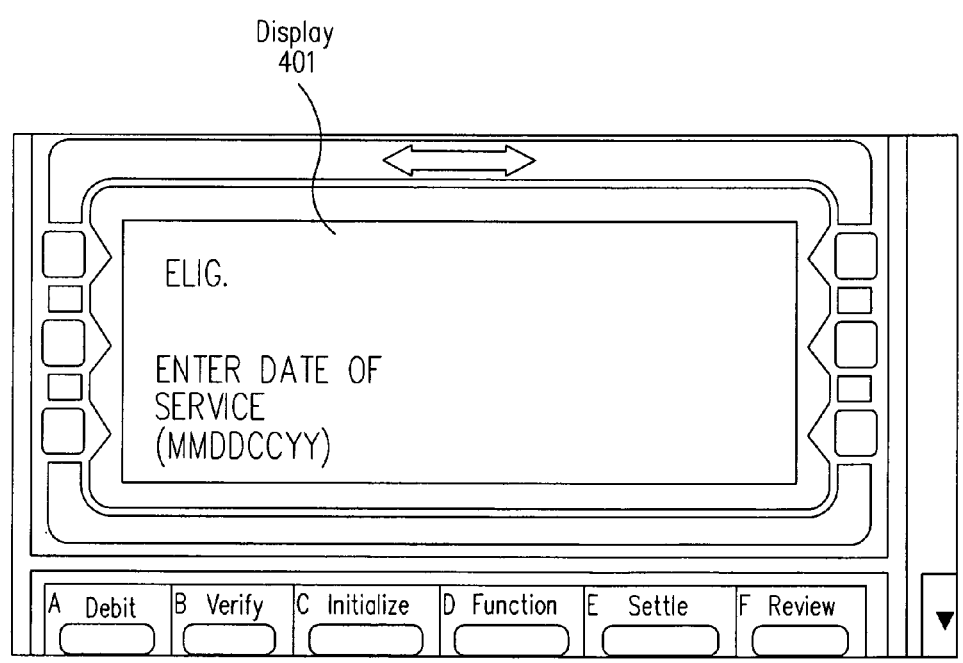

For example FIG. 5A illustrates beginning the transaction, a "HEALTHCARE" transaction service that is shown on display 401 is selected when a healthcare provider 120 presses key 403f. Key 403b is then pushed by healthcare provider 120 to select obtaining eligibility information that is labeled "ELIGIBILITY" in display 401 adjacent to key 403b. Healthcare provider 120 then swipes or passes card 121 through slot 405 in order to read information stored on card 121 as shown in FIG. 5C. A healthcare provider ID is then input to processing device 101b by entering the healthcare provider ID by way of keypad 402. An Enter button located in the lower right portion of the keypad 402 then may be pressed. In an alternate embodiment, a payer ID may be keyed by way of keypad 402. FIG. 5D illustrates a healthcare provider 120 selecting a healthcare recipient type, such as self, spouse, child or other by pressing keys 403b, 403c, 403e or 403f. FIGS. 5E-5F illustrate a healthcare provider 120 entering the healthcare recipient date of birth and date of service (healthcare), followed by pressing the enter button. As illustrated by logic block 207 in FIG. 2 and printout 404 of FIG. 4, eligibility information is then provided to healthcare provider 120 after a payer processing device receives the eligibility request and provides the eligibility response. In an embodiment, print out 404 then provides eligibility information similar to eligibility information 360 described above.

In an embodiment, processing device 101b generates an eligibility request that is a HIPAA-compliant 270 transaction and receives an eligibility response that is HIPAA-compliant 271 In an embodiment, an eligibility response is received by processing device 101b within 10 seconds of generating the eligibility request.

In method 200, eligibility requests are provided to an entity processing device as illustrated by logic block 203. In an embodiment, entity processing device 102 receives and routes an eligibility request in response to executing routing software 142 and a payer ID in an eligibility request. In an embodiment, routing software 142 includes a plurality of payer IDs and corresponding IP addresses of payer processing devices or Web sites. Router software 142 routes an eligibility request from processing devices 101*a/b* to payer processing device 103 located at the IP address associated with the payer ID in an eligibility request.

In logic block 204, payer processing device 103 executes eligibility rules software component 143 in response to receiving the eligibility request from the healthcare provider processing device 101*a/b* (via entity processing device 102) to determine an eligibility response including eligibility information. In an embodiment, each payer processing device 103 has different eligibility rules software to provide different eligibility information.

In logic block 205, payer processing device 103 generates an eligibility response to entity processing device 102 that forwards the eligibility response to healthcare processing device 101*a/b* as illustrated in logic block 206. In an embodiment, routing software 142 keeps track of pending eligibility requests so that processing device 102 may route the eligibility response to the appropriate IP address (or other address) of the healthcare processing device 101*a/b*.

In logic block 208, information to obtain medical information, such as a URL, user identifier and user password, is read. In an embodiment, the information is read from a magnetic strip of card 121 by wedge 130 so that processing device 101*a* may access medical information of healthcare recipient 122 that may be stored on another processing device, such as processing device 902. FIG. 3C illustrates medical information (or a health record) provided on Web page 380 for healthcare recipient 122, such as "Jane Doe". The medical information may include registration information 381, patient information 382, medications 383, conditions/medical history 384 and allergies 385 in an embodiment. Medical information is then accessed as illustrated by logic block 209. In an embodiment, application software 141 causes a browser stored on processing device 101*a* to access a URL stored on a magnetic strip of card 121. Application software 141 then enters a user identifier and password into a Web page (site) identified by the URL in order to access the medical information, such as medical information shown on Web page 380.

FIG. 6 illustrates a method 600 to allow an individual (such as healthcare recipient 122, family member, caregiver) to customize card 121 having user selected medical information and/or information to obtain medical information and/or eligibility of healthcare payments according to an embodiment. An individual can determine what medical information is provided and/or displayed on card 121 and where detailed medical information or an electronic personal health record is located on the Internet. In an embodiment, important or critical medical information, such as medications, allergies, and major illnesses, is selected by an individual or user to be displayed on card 121. A user customizes card 121 before healthcare is provided in an embodiment. In logic blocks 601 and 602, medical information of an individual, such as a healthcare recipient 122, is obtained and stored in a machine readable/executable or electronic format. In an embodiment, the medical information is in the form and obtained by way of "an electronic personal health record" as described in the above referenced U.S. patent application Ser. No. 11/208,144 filed Aug. 19, 2005 entitled "ELECTRONIC PERSONAL HEALTH RECORD SYSTEM." In an embodiment, card 121 is customized by a user at the end of "a registration process" as described in the above referenced U.S. patent application Ser. No. 11/208,144 filed Aug. 19, 2005 entitled "ELECTRONIC PERSONAL HEALTH RECORD SYSTEM."

In an embodiment, a coupon having a coupon code for a card 121 or a discount in purchasing card 121 is obtained as illustrated by logic block 603. In an embodiment, a payer or sponsor, such as a university or HMO, provides a coupon.

Logic blocks 604 illustrate providing a graphical user interface, or Web page 700, to allow a user or individual to select customizing a card 121 by clicking on "iHealthcard" simulated button 701. In an embodiment, Web page 700 is provided to a user at the end of a registration in which "an electronic personal health record", as described above, is created, maintained and/or updated. After iHealthcard simulated button 701 is clicked or selected by a user, graphical user interface, or Web page 710 as shown in FIG. 7B, is provided to a user. In an embodiment, software 902*b* obtains the medical information associated with the user from software/database 902*a* of processing device 902 and provides Web page 710 having the user's associated medical information.

A user may obtain a discounted or free card 121 by entering in a coupon code to field 713. A user then selects the medical information to be displayed on card 121 by clicking on the check box fields associated with the user's medical information stored in software/database 902*a* as illustrated by logic block 605. In particular, a user selects the user's medical information associated with categories: emergency contacts 714, clinicians 715, medications 716, conditions 717, allergies 718 and/or insurance 719, singly or in combination.

A simulation of card 121 as shown by graphics display or simulated card 723*a-b* then may be shown to the user in response to the user selecting the simulated "Save and Preview" button 712 as illustrated by logic block 606. As can be seen in simulated card 723*a-b*, certain medical information is not displayed as selected by a user. For example, an "Arthritis" condition is not displayed and will not ultimately be printed on card 121. In an embodiment, a logo of a sponsor or payer is provided in field 722 of the simulated card 723. In an embodiment, both the front and back of card 121 (723*a-b*) is provided as simulated card 723. When a user is satisfied with what medical information is displayed by way of viewing simulated card 723, a user may click on "Order iHealthcard" simulated button 720 as illustrated by logic block 607. In an embodiment, a JavaScript in software 902*b* is used to provide a simulation of card 121.

User customized medical information (or a portion of medical information) is then displayed or printed on card 121 as illustrated by logic block 608. Information to access remotely stored medical information and/or information to obtain eligibility of healthcare payments is recorded magnetically, electronically or by bar code on card 121 as illustrated by logic block 609. In an embodiment, a URL, user identifier and user password that identifies (as well as enables access) the location of medical information on the Internet is recorded on card 121. In an embodiment, information to obtain eligibility of healthcare payments is recorded as described below in regard to Table A and illustrated in FIGS. 3A-B and 9.

Logic block 610 illustrates charging a user based on a coupon in an embodiment. Web pages 730 and 740 as shown in FIGS. 7C-D are provided to a user in order to acknowledge a valid coupon and obtain credit card information, respectively.

Method 600 ends by providing a user, sponsor or partner with card 121 having user selected displayed medical information and/or recorded information to obtain remotely stored medical information and/or eligibility of healthcare payments. In an embodiment and as illustrated by logic block 611, a customized card is provided to a user by U.S. mail within one week.

Figure 8A:
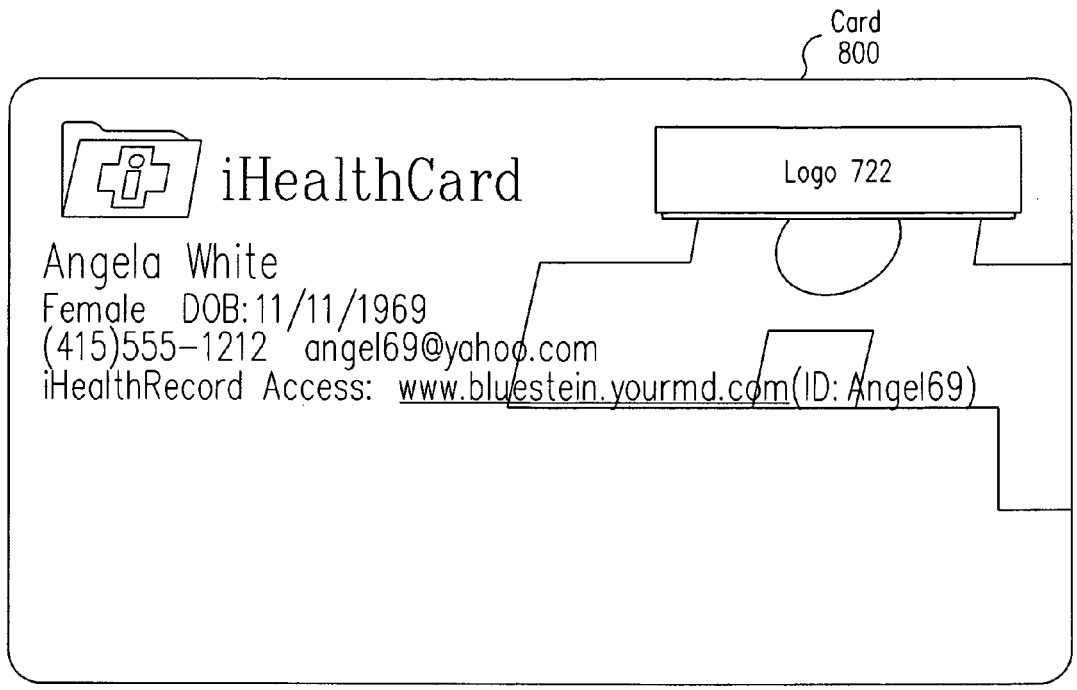
FIGS. 8A-C illustrate a card having medical information and information to obtain eligibility of healthcare payments according to embodiments of the invention.
Figure 8B:
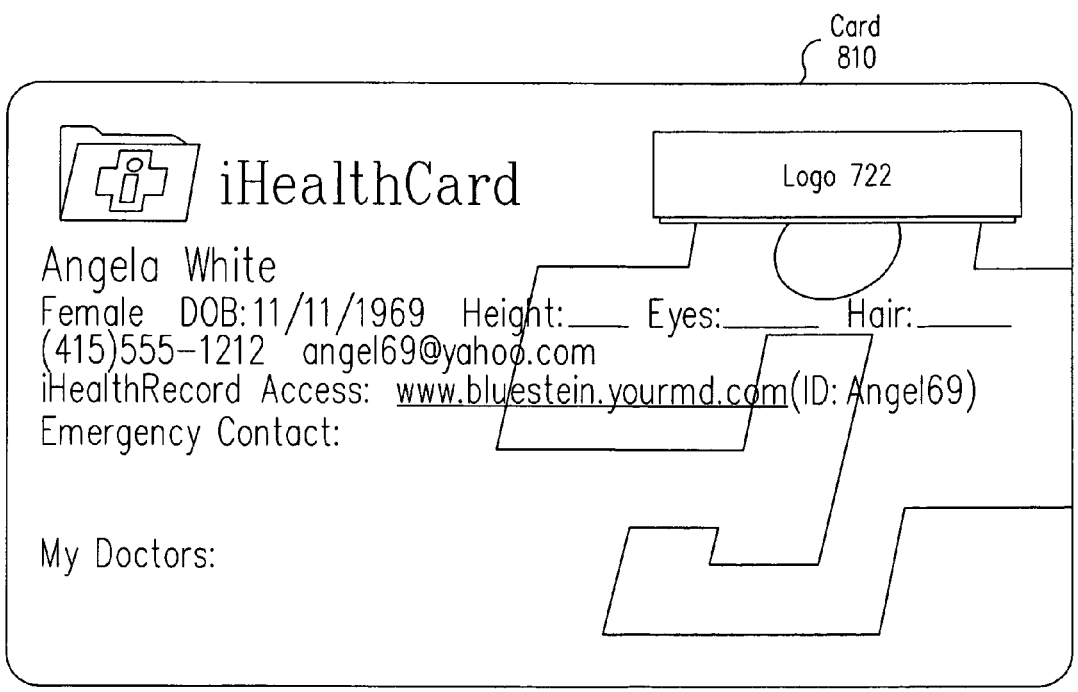
Figure 8C:
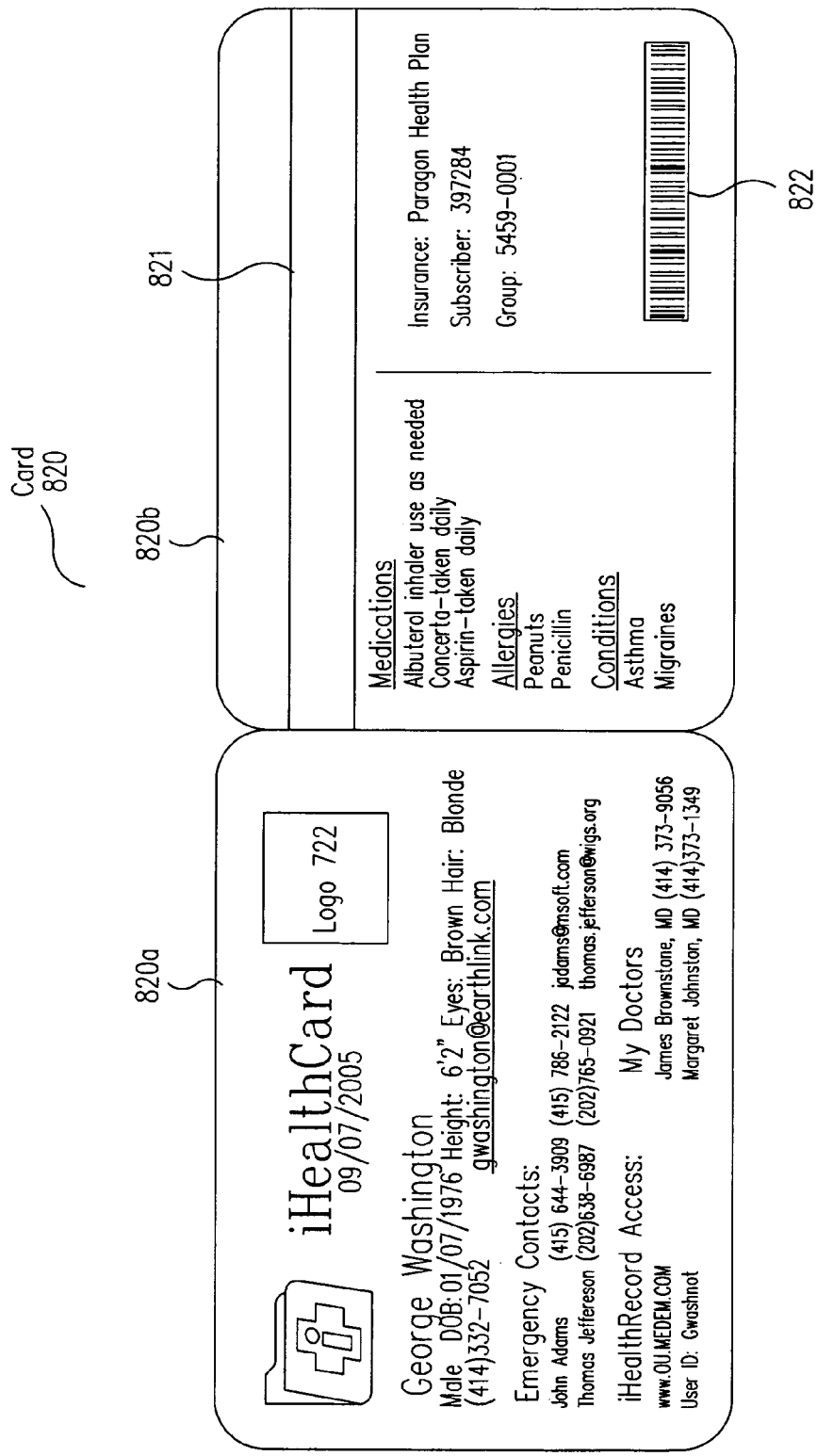

FIGS. 8A-C illustrate a card having displayed medical information and information to obtain remotely stored medical information and eligibility of healthcare payments that is provided to a healthcare recipient 122 according to embodiments. In an embodiment, cards 800 and 810 correspond to card 121. In an embodiment, FIG. 8A illustrates a front of a card 800 where header labels are not shown while FIG. 8B illustrates a card 810 where header labels are shown. For example, Angela White's "Height," "Eyes," "Hair," "Emergency Contact" and "My Doctors" header labels are not shown in card 800 where labels are shown in card 810. In an embodiment, the medical information or personal information associated with the header labels is recorded magnetically (by way of the magnetic strip), electronically or by bar codes. Header labels are not shown in order to increase confidentiality and security of the information. In an embodiment, a user may select whether header labels are displayed on card 121 as illustrated by logic block 605 above.

FIG. 8C illustrates a card 820 having a front 820a and a back 820b. In an embodiment, card 820 corresponds to card 121. Information to obtain remotely stored medical information and information to obtain eligibility of healthcare payments may be recorded on magnetic strip 821 and/or on bar codes 822. In an alternate embodiment, information to obtain remotely stored medical information and information to obtain eligibility of healthcare payments is recorded electronically or on an integrated circuit memory device disposed on card 820. In an embodiment, general medical information (including header labels) is displayed on front 820a along with sponsor logo 722. In an embodiment, critical medical information or medical information (along with header labels) selected by the user is displayed on back 820b.

In an embodiment, card 820 is a "wallet card" as described in the above referenced U.S. patent application Ser. No. 11/208,144 filed Aug. 19, 2005 entitled "ELECTRONIC PERSONAL HEALTH RECORD SYSTEM."

In an embodiment, card 820 is a 30 mil plastic (or laminated) card which is an industry standard for the merchant credit card industry. In embodiments, track 3 of the magnetic strip 821 on card 820 is encoded with payer and healthcare recipient information including: payer ID, subscriber ID, subscriber date of birth, subscriber Name and/or group/policy number, singly or in combination. A subscriber may be a healthcare recipient 122, family member or caregiver in embodiments.

In an embodiment, field numbers, field names, field lengths and characters for track 3 of magnetic strip 821 of card 820 is shown in Table A below.

TABLE A

| Field Number | Field Name | Field Length | Character |
|---|---|---|---|
| 0 | Start Code | N/A | — |
| 1 | Start Sentinel | 1 | % |
| 2 | Format Code | 1 | H |
| 3 | Payer ID | 10 | Alpha/Numeric |
| 4 | Field Separator | 1 | ^ |
| 5 | Subscriber ID | 20 | Alpha/Numeric |
| 6 | Field Separator | 1 | ^ |
| 7 | Subscriber DOB | 8 | Numeric |
| 8 | Subscriber Name | 26 | Alpha/Numeric |
| 9 | Field Separator | 1 | ^ |
| 10 | Group/Policy # | 11 | Alpha/Numeric |
| 11 | End Sentinel | 1 | ? |
| 12 | LRC | 1 | |
| | Total Length | 82 | |

In an embodiment, card 820 and in particular magnetic strip 821 includes information for financial transactions and/or to integrate with a healthcare institution's internal systems such as an electronic medical records (EMR) system software and admissions, discharge and transfer (ADT) system software.

In an embodiment, card 820 and in particular magnetic strip 821 includes a URL, user identifier and user password recorded consecutively on a predetermined track in an Alpha/Numeric format separated by field separators.

FIG. 9 illustrates a system 900 for converting and categorizing paper medical information according to an embodiment. FIG. 9 illustrates user (or individual) processing device 901, healthcare processing device 101a, and processing device 902 coupled to Internet 903. In an embodiment, processing devices 901, 101a and 902 transfer information over Internet 903 as described above. In an embodiment, processing device 902 stores and executes user card customizing software 902b and healthcare recipient electronic medical information database/software 902a that accesses medical information of healthcare recipient 122 stored on processing device 902. In an embodiment, method 600 illustrates, at least in part, the operation of software 902b. In particular, user 910 operates processing device 901 to store medical information (executing software 902a) in processing device 902 and customize card 121 (executing software 902b). User 910 may also provide paper medical information 920 to operators of processing device 902 so that the paper medical information 920 can be converted into a machine readable (or electronic) form and categorized by database/software 902a for respective healthcare recipients.

In an embodiment, a user will be given a unique user identifier and password for facsimile transmission (fax) of paper medical information 920 to processing device 902, which will direct their healthcare information into and populate the medical information, or health record, associated with the individual.

FIG. 10 illustrates a method 1000 that converts paper medical information 920 into machine readable/electronic form and categorizes the converted information for each healthcare recipient in software/database 902a. Method 1000 begins by a user 910 (or individual) obtaining medical information for an individual or healthcare recipient as illustrated by logic block 1001. The paper information is converted to machine readable/electronic format as illustrated by logic block 1002. In an embodiment, user 910 scans paper medical information 920 and e-mails the scanned paper medical information 920 to operators of processing device 902. In an alternate embodiment, user 910 faxes the paper medical information 920 using a unique user identifier and password to processing device 902. In an alternate embodiment, paper medical information 920 is mailed to operators of processing device 902 who then convert the faxes to machine readable format.

Logic block 1003 illustrates storing the converted paper medical information into a machine readable (electronic) format viewable and/or accessible by the healthcare recipient. In an embodiment, software 902a in response to selections from a healthcare recipient stores and sorts, as illustrated by logic block 1004, the converted paper medical information that is viewable from processing device 902 into medical categories associated with the healthcare recipient. In an alternate embodiment, a healthcare recipient sorts and categorizes converted paper medical information in their associated medical information, or health record, by way of a user interface, or Web page. In an embodiment, the converted paper medical information may be stored in categories such as lab reports, diagnostic reports, clinical summaries, EKGs, images, advanced directive and/or other patient specific information.

In an embodiment, user 910 will be charged a fee for converting paper medical information 920 into machine readable/electronic and category sorted form as shown by logic block 1007.

In an embodiment, a user 910 may customize a card 121 as illustrated by logic block 1005 and similar to logic blocks 604-605 in method 600. A simulation of card 121 may be provided to user 910 and a user 910 may select other categories when the simulation of card 121 is not satisfactory as illustrated by logic block 1006 in an embodiment and as similarly described in method 600 of FIG. 6.

Method 1000 ends by providing a customized card 121 to user 910 as illustrated in logic blocks 1008 and as similarly described in method 600 of FIG. 6.

Figure 11:
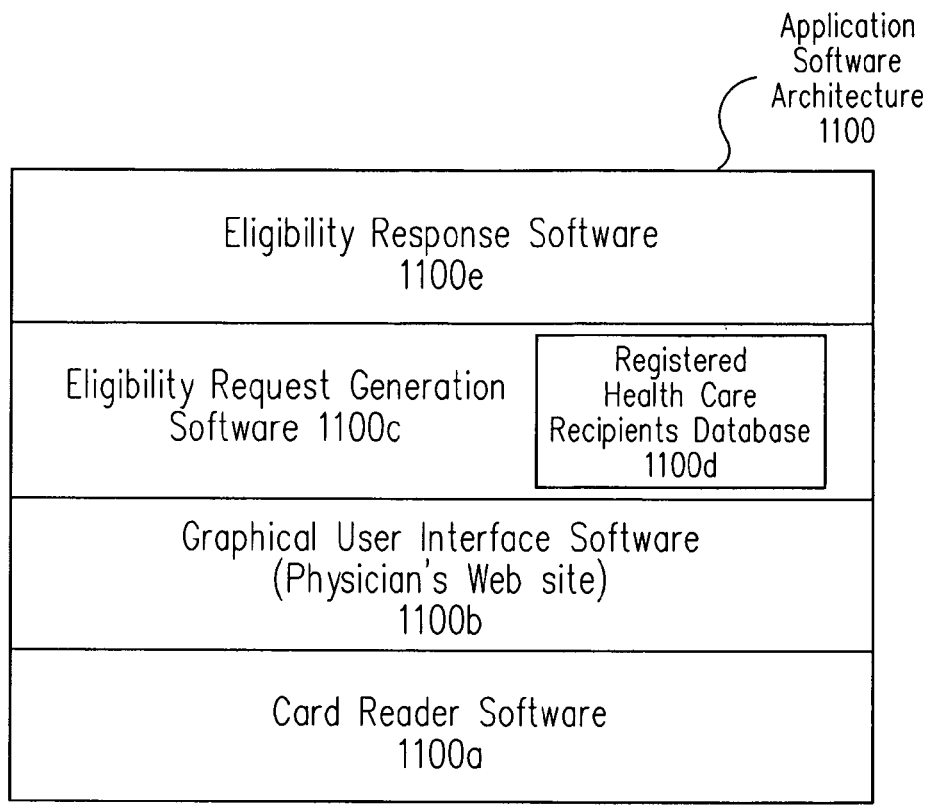
FIG. 11 illustrates application software architecture according to an embodiment.
Figure 12:
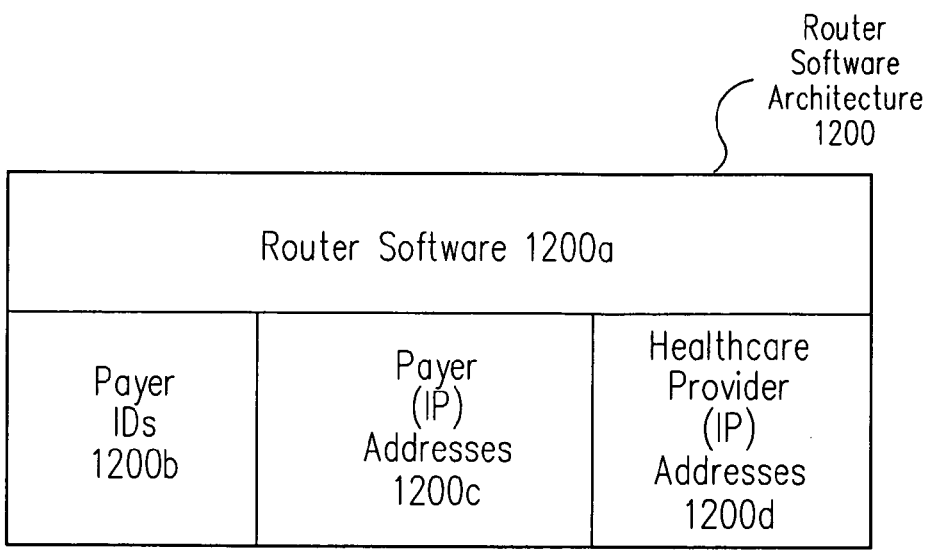
FIG. 12 illustrates router software architecture according to an embodiment.
Figure 13:
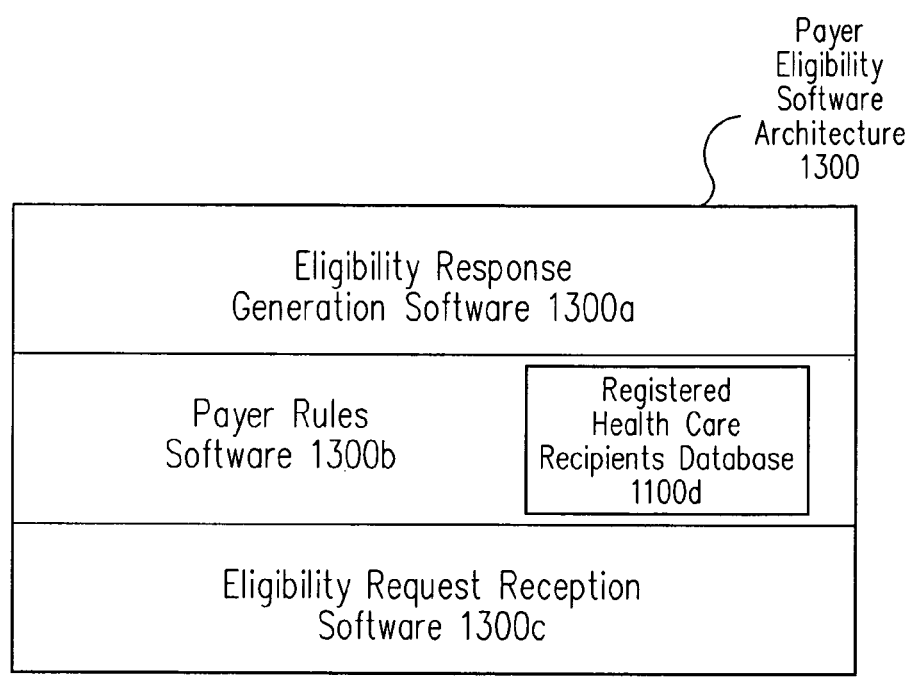
FIG. 13 illustrates payer eligibility software architecture according to an embodiment.

FIGS. 11-13 illustrate software architectures that represent software stored and/or executed on processing devices described herein. Software, singly or in combination, may be stored on an article of manufacture, such as a computer (or machine) readable medium, that are included or associated with the processing devices described herein. For example, software may be stored in a magnetic hard disk, a magnetic tape, an optical disk, a floppy disk, Compact Disk Read-Only Memory (CD-ROM), an integrated circuit memory device such as Random Access Memory (RAM), Read-Only Memory (ROM), Electrically Erasable Programmable Read-Only Memory (EEPROM) or other readable or writeable data storage technologies, singly or in combination.

FIG. 11 illustrates application software architecture 1100 according to an embodiment. Application software architecture 1100 includes eligibility response software 1100e, eligibility request generation software 1100c, registered healthcare recipients database 1100d, graphical user interface (for example, a physician web site) software 1100b and card reader software 1100a that is stored and executed on processing device 101a. In an embodiment, application software architecture 1100 corresponds to software 141 shown in FIG. 1.

Card reader software 1100a is responsible for reading information to obtain remotely stored medical information and information to obtain eligibility of healthcare payments from card 121. The information to obtain medical information and information to obtain eligibility of healthcare payments may be stored on card 121 in a magnetic bar code and/or electronic form. In an embodiment, card reader software 1100a obtains an address, such as a URL, and causes a browser to access the web site identified by the address. Card reader software 1100a then reads a user identifier and password from card 121 so that the user identifier and password values may be entered into the appropriate fields at the web site identified by the URL thereby enabling access of medical information by a healthcare provider.

Graphical user interface software 1100b is responsible for providing the medical information and eligibility of healthcare payments information to a healthcare provider. Graphical user interface software 1100b is also responsible for allowing a user, such as a healthcare provider, to enter and update medical information. Likewise, Graphical user interface software 1100b is responsible for allowing a user to register. Graphical user interface software 1100b is also responsible for allowing the user to enter and view information associated with an eligibility request and/or eligibility response. In an embodiment, Graphical user interface software 1100b provides Web pages 300, 350 and 380 shown in FIGS. 3A-C.

Eligibility request generation software 1100c is responsible for generating an eligibility request to payer processing device 103 via entity processing device 102 in an embodiment. An eligibility request may include the information shown in Table A above, singly or in combination that has been retrieved from card 121. In an embodiment, eligibility request generation software 1100c compares a subscriber ID read from card 121 with subscriber IDs that have been registered and stored in registered healthcare recipient software/database 1000d. In an alternate embodiment, processing device 101a accesses processing device 902 to determine whether the read subscriber ID from card 121 matches registered healthcare recipients associated with healthcare provider 120 before an eligibility request is generated.

Eligibility response software 1100e is responsible for receiving eligibility responses from payer processing device 103 (via entity processing device 102) in response to previously sent eligibility requests.

FIG. 12 illustrates router software architecture 1200 according to an embodiment. Router software architecture 1200 includes router software 1200a, payer IDs 1200b, Payer (IP) addresses 1200c and Healthcare provider (IP) addresses 1200d that are stored and executed on processing device 102. In an embodiment, router software architecture 1200 corresponds to router software 142 shown in FIG. 1. In an embodiment, router software 1200a uses a payer ID in a received eligibility request from processing device 101a/b and selects the corresponding payer address in Payer (IP) addresses 1200c to route the eligibility request to the location of payer processing device 103. In an embodiment, payer IDs 1200b are a list of payer IDs that have associated payer addresses in Payer (IP) addresses 1200c. In an embodiment, payer addresses, as well as healthcare provider (IP) addresses, are IP addresses to respective payer and Healthcare processing devices. Similarly, router software 1200a routes an eligibility response to the appropriate healthcare processing device by using Healthcare processing addresses 1200d to reroute the eligibility response from payer processing device 103 to healthcare processing device 101a/b. In an embodiment, router software 1200a maintains a queue of outstanding eligibility requests and associated healthcare provider addresses in order to know where to route the outstanding eligibility response.

FIG. 13 illustrates payer eligibility software architecture 1300 according to an embodiment. Payer eligibility software architecture 1300 includes eligibility request reception software 1300c, payer rules software 1300b, and eligibility response generation software 1300a that is stored and executed on processing device 103. In an embodiment, payer eligibility software architecture 1300 corresponds to payer eligibility rules software 143 shown in FIG. 1.

Eligibility request reception software 1300c is responsible for receiving an eligibility request from entity processing device 102 in an embodiment. Eligibility request reception software 1300c parses the eligibility request and passes the information to payer rules software 1300b. In an embodiment, payer rules software 1300b determines the eligibility information for a particular healthcare recipient at a particular time. In an embodiment, payer rules software 1300baccesses a list in registered healthcare recipients' database 1100d associated with the healthcare provider that is stored at payer processing device 103 and compares a received subscriber ID in a received eligibility request with the list in order to determine whether the healthcare recipient is eligible for healthcare payments. When a received subscriber ID matches an entry on the list, payer rules software 1300b provides eligibility information to eligibility response generation software 1300a. Eligibility response generation software 1300 a then generates an eligibility response including eligibility information to healthcare processing device 101a/b (via entity processing device 102) in response to the output of payer rules software 1300b.

The foregoing description of the preferred embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A system comprising:
a first processing device to obtain information to access medical information of an individual and information to obtain eligibility of payment of healthcare for the individual, the information to access the medical information of the individual and information to obtain eligibility recorded on the plastic card, the first processing device to generate an eligibility request in response to reading the information to obtain eligibility recorded on the plastic card, the first processing device to obtain the medical information in response to reading the information to access the medical information;
a second processing device, coupled to the first processing device, to receive and route the eligibility request, the second processing device routes the eligibility request in response to an identifier in the eligibility request;
a third processing device, coupled to the second processing device, to receive the eligibility request, the third processing device to provide an eligibility response to the first processing device by way of the second processing device, the eligibility response including eligibility information of payment of healthcare for the individual; and a fourth processing device, coupled to the first processing device, to provide the medical information to the first processing device in response to the information to access the medical information;
wherein the fourth processing device comprises:
a storage device to store the medical information of the individual;
a processor, coupled to the storage device;
the storage device to store executable instructions for controlling the processor; and the processor is operative with the executable instructions to:
receive a request to provide a card displaying a portion of the medical information of the individual;
provide a graphical user interface allowing the individual to select a first portion of the medical information, wherein the first portion of the medical information is to be displayed on the card; and
receive a selection from the individual that indicates the first portion.

2. The system of claim 1, wherein the information to access the medical information includes a URL, user identifier and password, and wherein the fourth processing device provides the medical information in response to receiving the user identifier and password.

3. The system of claim 2, wherein the individual is a healthcare recipient and the medical information includes information selected from a group consisting of a name of the individual, an individual to contact in case of emergency, a clinician used by the individual, a medication taken by the individual, a medical condition of the individual, and an allergy of the individual.

4. The system of claim 1, wherein the substrate is a plastic card having a magnetic strip, and wherein the information to access the medical information is recorded on the magnetic strip, and wherein the information to obtain eligibility is recorded on the magnetic strip.

5. The system of claim 1, wherein the processor is operative with the executable instructions to simulate the card.

6. The system of claim 1, wherein the card is an article of manufacture including a magnetic readable medium, comprising:
a first field to store information that indicates a payer of health care of the individual;
a second field to store information that identifies the individual; and
a third field to store information that indicates a policy number associated with the individual.

7. The article of manufacture of claim 6, wherein the first, second, and third fields are positioned on a track of the magnetic strip.

8. The system of claim 7, wherein the substrate is a card, and wherein the first processing device includes a card reader.

* * * * *